(12) United States Patent
McGrath et al.

(10) Patent No.: US 10,188,992 B2
(45) Date of Patent: Jan. 29, 2019

(54) POLYBENZIMIDAZOLES AND METHODS OF MAKING AND USING THEREOF

(71) Applicants: BOARD OF REGENTS, THE UNIVERSITY OF TEXAS SYSTEM, Austin, TX (US); Virginia Tech Intellectual Properties, Inc., Blacksburg, VA (US)

(72) Inventors: James E. McGrath, Blacksburg, VA (US); Judy S. Riffle, Blacksburg, VA (US); Benny D. Freeman, Austin, TX (US)

(73) Assignees: Board of Regents, The University of Texas System, Austin, TX (US); Virginia Tech Intellectual Properties, Inc., Blacksburg, VA (US)

(*) Notice: Subject to any disclaimer, the term of this patent is extended or adjusted under 35 U.S.C. 154(b) by 61 days.

Patent file contains an affidavit/declaration under 37 CFR 1.130(b).

(21) Appl. No.: 15/269,101

(22) Filed: Sep. 19, 2016

(65) Prior Publication Data

US 2017/0081477 A1 Mar. 23, 2017

Related U.S. Application Data

(60) Provisional application No. 62/220,478, filed on Sep. 18, 2015.

(51) Int. Cl.
*B01D 53/22* (2006.01)
*B01D 71/68* (2006.01)
(Continued)

(52) U.S. Cl.
CPC .......... *B01D 71/68* (2013.01); *B01D 53/228* (2013.01); *B01D 71/62* (2013.01); *C07C 315/04* (2013.01);
(Continued)

(58) Field of Classification Search
CPC ...... B01D 53/228; B01D 71/62; B01D 71/68; B01D 2256/16; B01D 2256/18;
(Continued)

(56) References Cited

U.S. PATENT DOCUMENTS

| | | | |
|---|---|---|---|
| 2009/0098437 A1* | 4/2009 | Choi | C08G 73/18 429/410 |
| 2011/0311745 A1* | 12/2011 | Yang | B01D 71/62 428/36.9 |
| 2016/0375410 A1* | 12/2016 | Berchtold | B01D 53/228 95/55 |

OTHER PUBLICATIONS

Borjigin, Hailun et al., "Synthesis and characterization of polybenzimidazoles derived from tetraaminodiphenylsulfone for high temperature gas separation membranes", Polymer, 71, 2015, pp. 135-142. (Year: 2015).*

(Continued)

*Primary Examiner* — Jason M Greene
(74) *Attorney, Agent, or Firm* — Meunier Carlin & Curfman LLC

(57) ABSTRACT

Disclosed are polybenzimidazoles containing sulfonyl groups. The polymers can be synthesized in Eaton's reagent from 3,3',4,4'-tetraaminodiphenylsulfone, which itself can be synthesized from 4,4'-dichlorodiphenylsulfone. Methods of synthesizing the polymers are disclosed. The disclosed polymers can be used for high temperature $H_2/CO_2$ separation membranes and other uses.

21 Claims, 7 Drawing Sheets

(51) Int. Cl.
  *C07C 315/04* (2006.01)
  *C08G 73/18* (2006.01)
  *B01D 71/62* (2006.01)
  *C08G 73/06* (2006.01)
(52) U.S. Cl.
  CPC .......... *C08G 73/18* (2013.01); *B01D 2256/16* (2013.01); *B01D 2256/18* (2013.01); *B01D 2257/104* (2013.01); *B01D 2257/108* (2013.01); *B01D 2257/11* (2013.01); *B01D 2257/504* (2013.01); *Y02C 10/10* (2013.01); *Y02P 20/152* (2015.11)
(58) Field of Classification Search
  CPC ........ B01D 2257/104; B01D 2257/108; B01D 2257/11; B01D 2257/504; C08G 73/18; C07C 315/00; C07C 315/04
  See application file for complete search history.

(56) References Cited

OTHER PUBLICATIONS

Kumbharkar, S.C. et al., "High performance polybenzimidazole based asymmetric hollow fibre membranes for H2/CO2 separation", Journal of Membrane Science, 375, 2011, pp. 231-240. (Year: 2011).*
Baker, et al., "Future Directions of Membrane Gas Separation Technology", Ind. Eng. Chem. Res 41(6), 2002; 1393-1411.
Berchtold, et al., "Polybenzimidazole composite membranes for high temperature synthesis gas separations", J Memb Sci 2012; 415-416:265-70.
Borjigin, et al., "Synthesis and Characterization of Thermally Rearranged (TR) Polybenzoxazoles: Influence of isomeric structure on gas transport properties", Polymer 75, 2015 199-210.
Brooks, et al., "An NMR study of absorbed water in polybenzimidazole", Polymer 1993; 34:4038-42.
Coleman, et al., "Isomeric polyimides based on fluorinated dianhydrides and diamines for gas separation applications", J Memb Sci 1990; 50:285-97.
Freeman, "Basis of Permeability/Selectivity Tradeoff Relations in Polymeric Gas Separation Membranes", Macromolecules 1999; 32:375-80.
Ghosal, et al., "Gas Separation Using Polymer Membranes : An Overview", Polym Adv Techologies 1994; 5:673-97.
Guo, et al., "Aromatic Polyethers, Polyetherketones, Polysulfides, and Polysulfones", Polym. Sci. Compr. Ref., vol. 5, Elsevier B.V.; 2012, doi :10.1016/B978-0-444-53349-4.00153-9; p. 377-430.
Jouanneau, et al., "Synthesis of Sulfonated Polybenzimidazoles from Functionalized Monomers : Preparation of Ionic Conducting Membranes", Macromolecules 2007; 40:983-90.
Klaehn, et al., "New Soluble N-Substituted Polybenzimidazoles by Post-Polymerization Modification", Polym Prepr 2005; 46:708-9.
Kumbharkar, et al., "Enhancement of gas permeation properties of polybenzimidazoles by systematic structure architecture", J Memb Sci 2006; 286:161-9.
Kumbharkar, et al., "High performance polybenzimidazole based asymmetric hollow fibre membranes for H2/CO2 separation", J Memb Sci 2011; 375:231-40.
Lakshmi, et al., "Polybenzimidazoles. VI. Polybenzimidazoles containing aryl sulfone linkages", J Polym Sci Part A-1 Polym Chem 1967; 5: 1113-8.
Li, et al., "Influence of polybenzimidazole main chain structure on H2/CO2 separation at elevated temperatures", J Memb Sci 2014; 461:59-68.
Li, et al., "Synthesis and Characterization of a New Fluorine-Containing Polybenzimidazole (PBI) for Proton-Conducting Membranes in Fuel Cells", Fuel Cells 2013; 13:832-42.
Lin, et al., "Permeation and Diffusion", Springer-handb. Mater. Meas. Methods, Springer; 2006, doi: 10.1007/978-3-540-30300-8_7; p. 371-87.
Mader, et al., "Sulfonated Polybenzimidazoles for High Temperature PEM Fuel Cells", Macromolecules 2010; 43:6706-15.
Menczel, "Thermal Measurements on Poly[2,2'-(m-phenylene)-5,5'-bibenzimidazole] Fibers", J Therm Anal Calorim 2000; 59:1023-7.
Merkel, "Carbon dioxide capture with membranes at an IGCC power plant", J Memb Sci 2012; 389:441-50.
Mi, et al., "Dependence of the gas permeability of some polyimide on their intrasegmental mobility", J Memb Sci 1993; 77:41-8.
O'Brien, et al., "Towards a pilot-scale membrane system for pre-combustion CO2 separation", Energy Procedia 2009; 1:287-94.
Pesiri, et al., "Thermal optimization of polybenzimidazole meniscus membranes for the separation of hydrogen, methane, and carbon dioxide", J Memb Sci 2003; 218:11-8.
Robeson, et al., "An empirical correlation of gas permeability and permselectivity in polymers and its theoretical basis", J Memb Sci 2009; 341:178-85.
Robeson, et al., "Correlation of separation factor versus permeability for polymeric membranes", J. Membr. Sci. 1991,62, (2), 165-185.
Robeson, et al., "High performance polymers for membrane separation", Polymer 1994;35:4970-8.
Robeson, et al., "The upper bound revisited", J Memb Sci 2008; 320:390-400.
Robeson, et al., "Synthesis and Dynamic Mechanical Characteristics of Poly(Aryl Ethers)", Appl Polym Symp 1975; 26:375-85.
Stern, "Polymers for gas separations: the next decade", J. Membr. Sci. 1994,94, (1), 1-65.
Tanaka, et al., "Effect of Methyl Substituents on Permeability and Permselectivity of Gases in Polyimides Prepared from Methyl-Substituted Phynylenediamines", J Polym Sci Part B Polym Phys 1992; 30:907-14.
Tanaka, et al., "Permeability and permselectivity of gases in fluorinated polyimides", Polymer 1992; 33:585-92.
Ueda, et al., "Poly(benzimidazole) synthesis by direct reaction of diacids and diamines", Macromolecules 1985; 18:2723-6.
Vogel, et al., "Polybenzimidazoles, new thermally stable polymers", J Polym Sci 1961; 50:511-39.
Narayan et al., Polybenzimidazoles. VI. Polybenzimidazoles Containing Aryl Sulfone Linkages, Journal of Polymer Science: Part A-1, vol. 5, pp. 1113,1118, 1967.

* cited by examiner

POLYBENZIMIDAZOLES AND METHODS OF MAKING AND USING THEREOF

ACKNOWLEDGEMENT OF GOVERNMENT SUPPORT

This invention was made with government support under grant numbers DMR1126564 and IIP1237857 awarded by the National Science Foundation. The government has certain rights in this invention.

BACKGROUND

Polymeric membranes for gas separation have become an important technology for various industrial refinery processes. In contrast to traditional separation technologies such as cryogenic distillation, pressure swing adsorption and chemical absorption, membrane separations offer several advantages, including lower energy consumption, lower capital investment, and ease of operation (see e.g., Stern S A. Polymers for gas separations: the next decade. *J Membr Sci* 1994; 94:1-64). Due to a significant growth in interest over the last ~30 years, numerous polymers have been developed as membranes for a variety of gas separations (see e.g., Baker R W. Future Directions of Membrane Gas Separation Technology. *Ind Eng Chem Res* 2002; 41:1393-411). An inherent trade-off relationship between permeability and gas selectivity based on empirical observations of available gas transport data has been reported by Robeson (Robeson L M. Correlation of separation factor versus permeability for polymeric membranes. *J Membr Sci* 1991; 62:165-85; Robeson L M, et al., High performance polymers for membrane separation. *Polymer* 1994; 35:4970-8) and the theory behind this phenomenon was described by Freeman (Freeman B D. Basis of Permeability/Selectivity Tradeoff Relations in Polymeric Gas Separation Membranes. *Macromolecules* 1999; 32:375-80). Most of the available gas transport data on polymeric membranes from research laboratories have been measured in the temperature range of 25-35° C. However, for many industrial applications, the ideal operating temperature may vary significantly from ambient conditions. For example, a high operation temperature (150-300° C.) is required to improve the thermal efficiency for $H_2$ separation from pre-combustion syngas in the Integrated Gasification Combustion Cycle (IGCC) system for electricity production (Merkel T C, et al., Carbon dioxide capture with membranes at an IGCC power plant. *J Membr Sci* 2012; 389:441-50; O'Brien K C, et al., Towards a pilot-scale membrane system for pre-combustion $CO_2$ separation. *Energy Procedia* 2009; 1:287-94). These harsh conditions eliminate most polymer membranes from consideration due to thermal instabilities that lead to degradation and loss of mechanical properties (Robeson L M, et al., Synthesis and Dynamic Mechanical Characteristics of Poly(Aryl Ethers). *Appl Polym Symp* 1975; 26:375-85).

Polybenzimidazoles (PBIs), initially developed by Marvel, are well known for their outstanding thermal stability, often exhibiting glass transition temperatures greater than 400° C. as well as flame retardance and chemical stability (Ueda M, et al., Poly(benzimidazole) synthesis by direct reaction of diacids and diamines. *Macromolecules* 1985; 18:2723-6; Vogel H, et al., Polybenzimidazoles, new thermally stable polymers. *J Polym Sci* 1961; 50:511-39). Due to these characteristics, they are promising candidates for gas separation membranes that can be used at high temperatures. Membranes prepared from a commercial polybenzimidazole, CELAZOLE™, have been shown to have attractive gas transport properties (Berchtold K A, et al., Polybenzimidazole composite membranes for high temperature synthesis gas separations. *J Membr Sci* 2012; 415-416: 265-70; Pesiri D R, et al., Thermal optimization of polybenzimidazole meniscus membranes for the separation of hydrogen, methane, and carbon dioxide. *J Membr Sci* 2003; 218:11-8). CELAZOLE™ (sometimes referred to as m-PBI in the literature) (Id.; O'Brien et al., *Energy Procedia* 2009; 1:287-94) is prepared from 3,3'-diaminobenzidine and isophthalic acid. However, polybenzimidazoles based on the 3,3'-diaminobenzidine monomer have very limited solubilities in common solvents due to their rigid rod structures and intermolecular hydrogen bonding (Li X, et al., Synthesis and Characterization of a New Fluorine-Containing Polybenzimidazole (PBI) for Proton-Conducting Membranes in Fuel Cells. *Fuel Cells* 2013; 13:832-42). For instance, m-PBI is only partially soluble in dimethylacetamide and insoluble in other common solvents, and PBIs based on 3,3'-diaminobenzidine and terephthalic acid are insoluble in common organic solvents (Vogel et al., *J Polym Sci* 1961; 50:511-39). Structural modification of polymer backbones to include flexible linkages usually increase the solubility of PBIs (Kumbharkar S C, et al., High performance polybenzimidazole based asymmetric hollow fibre membranes for $H_2/CO_2$ separation. *J Membr Sci* 2011; 375:231-40). However, a reduction in rigidity causes a decrease in the glass transition temperature, thus compromising the high temperature properties of these glassy polymers (Kumbharkar S C, et al., Enhancement of gas permeation properties of polybenzimidazoles by systematic structure architecture. *J Membr Sci* 2006; 286:161-9). What are thus needed are new synthetic methods towards PBIs as well as new PBI derivatives. The compositions and methods disclosed herein address these and other needs.

SUMMARY

In accordance with the purposes of the disclosed materials, compounds, compositions, articles, devices, and methods, as embodied and broadly described herein, the disclosed subject matter relates to compositions and methods of making and using the compositions. In other aspects, the disclosed subject matter relates to polymers comprising Formula I.

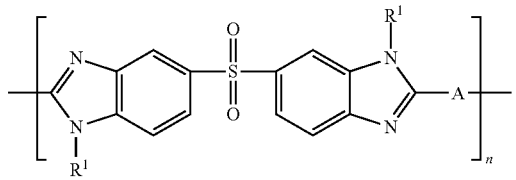

Formula I wherein
A can be an aryl or heteroaryl containing moiety;
$R^1$ can be H or substituted or unsubstituted $C_{1-20}$ alkyl, substituted or unsubstituted $COC_{1-20}$ alkyl, substituted or unsubstituted $CO_2C_{1-20}$ alkyl, substituted or unsubstituted $CO_2$ aryl, substituted or unsubstituted $CO_2C_{1-6}$ alkylaryl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, or mixtures thereof, wherein the substituted groups are substituted with one or more of alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol groups; and n can be from 2 to 200,000.

The polymers disclosed herein can be homopolymers, graft copolymers, or block copolymers, any of which can be crosslinked or uncrosslinked. The polymers disclosed herein can also be formed into thin films that can be applied to a substrate.

Also disclosed herein are methods of synthesizing polymers that comprise contacting 3,3',4,4'-tetraaminodiphenylsulfone with a polycarboxylic acid, salt thereof, or activated ester thereof, in the presence of phosphorus pentoxide and methanesulfonic acid. In specific examples, 3,3',4,4'-tetraaminodiphenylsulfone can be contacted with an aryl or heteroaryl dicarboxylic acid, salt thereof, or activated ester thereof, to produce polymers as disclosed herein.

In still further examples, disclosed herein are methods of synthesizing 3,3',4,4'-tetraaminodiphenylsulfone that comprise contacting dichlorodiphenylsulfone with a nitration reagent, to thereby provide a dinitrodichlorodiphenylsulfone; contacting the dinitrodichlorodiphenylsulfone with an amination reagent, to thereby provide dinitrodiaminodiphenylsulfone; and contacting the dinitrodiaminodiphenylsulfone with a reducing reagent, to thereby provide 3,3',4,4'-tetraaminodiphenylsulfone. In certain examples, the nitration reagent can comprise nitric acid, the amination reagent can comprise ammonium, and the reducing reagent can comprise hydrogen with palladium catalyst.

Methods of preparing the polymers disclosed herein can also include the steps of preparing 3,3',4,4'-tetraaminodiphenylsulfone as disclosed herein.

In still other examples, disclosed herein are methods of separating $H_2$ and $CO_2$ from a stream, that comprise contacting the stream with a polymer as disclosed herein.

Additional advantages of the disclosed subject matter will be set forth in part in the description that follows and the Figures, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

DETAILED DESCRIPTION

Figure 1:
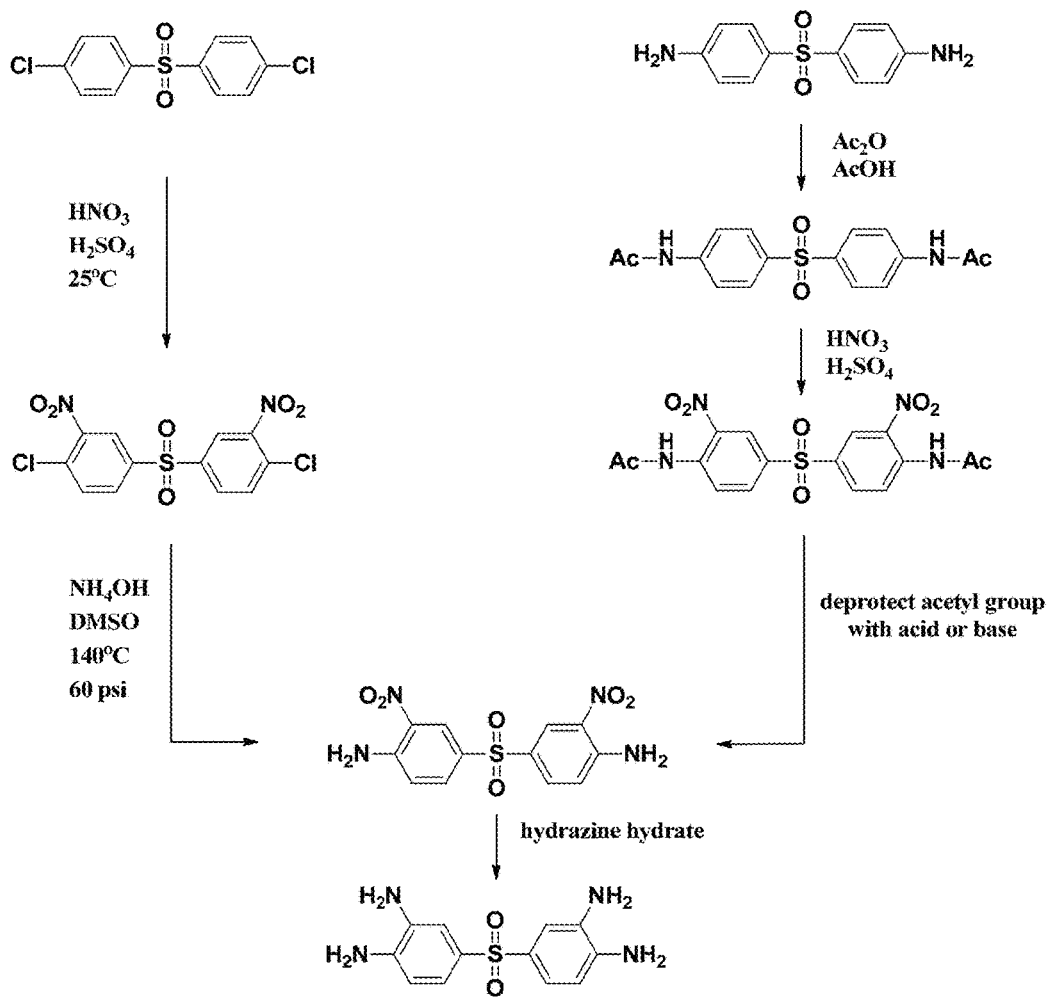
FIG. 1 shows routes for TADPS synthesis.

The materials, compounds, compositions, articles, and methods described herein may be understood more readily by reference to the following detailed description of specific aspects of the disclosed subject matter and the Examples and Figures included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value.

When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halides, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms with a structural formula containing at least one carbon-carbon double bond.

Asymmetric structures such as ($Z^1Z^2$)C=C($Z^3Z^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C=O, which is also referred to herein as a "carbonyl."

The terms "amine" or "amino" as used herein are represented by the formula —NZ$^1$Z$^2$, where Z$^1$ and Z$^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —C(O)NZ$^1$Z$^2$.

The term "carboxylic acid" as used herein is represented by the formula —C(O)OH. A "carboxylate" or "carboxyl" group as used herein is represented by the formula —C(O)O$^-$.

The term "ester" as used herein is represented by the formula —OC(O)Z$^1$ or —C(O)OZ$^1$, where Z$^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula Z$^1$OZ$^2$, where Z$^1$ and Z$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula Z$^1$C(O)Z$^2$, where Z$^1$ and Z$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —NO$_2$.

The term "silyl" as used herein is represented by the formula —SiZ$^1$Z$^2$Z$^3$, where Z$^1$, Z$^2$, and Z$^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2$Z$^1$, where Z$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "thiol" as used herein is represented by the formula —SH.

The term "thio" as used herein is represented by the formula —S—.

"R$^1$," "R$^2$," "R$^3$," "R$^n$," etc., where n is some integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

The expression "nitration reagent" refers to a reagent or a mixture of reagents that can add a nitro group to an aryl by electrophilic substitution. Examples of nitration reagents include nitric acid, a mixture of nitric acid and sulfuric acid (HNO$_3$/H$_2$SO$_4$), a mixture of one or more of NaNO$_3$, NaNO$_3$ or CuNO$_3$ with one or more acids selected from hydrochloric acid, hydrobromic acid, sulfuric acid, and nitric acid, a mixture of NaNO$_2$ and acetic acid, N$_2$O$_5$/P$_2$O$_5$/CCl$_4$, HONO, EtONO$_2$, CH$_3$COONO$_2$, NO$_2$ with CF$_3$SO$_3$, and Vanadium(v) oxytrinitrate (VO(NO$_3$)$_3$).

The expression "amination reagent" refers to a reagent or a mixture of reagents that can add an amine group to an aryl by nucleophilic substitution. Examples of amination reagents include ammonium hydroxide, ammonium carbonate, ammonium bicarbonate, ammonium phosphate, and O-mesitylenesulfonylhydroxylamine.

The expression "reducing reagent" refers to a reagent or a mixture of reagents that can reduce a nitroaryl to an aryl amine. Examples of reducing reagents include hydrogen with palladium catalyst (e.g., palladium on carbon, palladium (II) acetate, allylpalladium(II) chloride dimer, di-g-chlorobis[(1,2,3-η)-1-phenyl-2-propenyl]dipalladium(II), cyclopentadienyl(allyl)palladium(II), cyclopentadienyl[(1,2,3-n)-1-phenyl-2-propenyl]palladium(II), palladium(II) chloride, palladium(II) pivlate, palladium(0)dba2, palladium (II) acetylacetonate, tetrakis(triphenylphosphine)palladium (0)), hydrogen with Rainey nickel catalyst, lithium aluminum hydride, diisobutylaluminum hydride, and sodium borohydride.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compounds

Disclosed herein are polybenzimidazoles with sulfonyl moieties. These polymers can be represented with Formula I or have a section or block represented by Formula I.

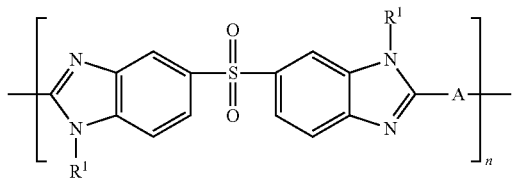

Formula I wherein

A can be an aryl or heteroaryl containing moiety;

$R^1$ can be H or substituted or unsubstituted $C_{1-20}$ alkyl, substituted or unsubstituted $COC_{1-20}$ alkyl, substituted or unsubstituted $CO_2C_{1-20}$ alkyl, substituted or unsubstituted $CO_2$ aryl, substituted or unsubstituted $CO_2C_{1-6}$ alkylaryl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, or mixtures thereof, wherein any of the substituted groups named can be substituted with one or more of alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol groups; and n can be from 2 to 200,000.

The disclosed polymers can be homopolymers, graft copolymers, or block copolymers. They can also be homopolymers, graft copolymers, or block copolymers that are linear or subsequently crosslinked after the linear polymer is formed.

In specific examples, the aryl containing moiety can be chosen from one or more of the following moieties:

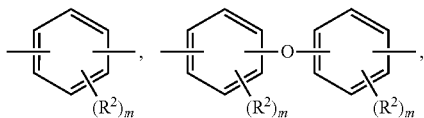

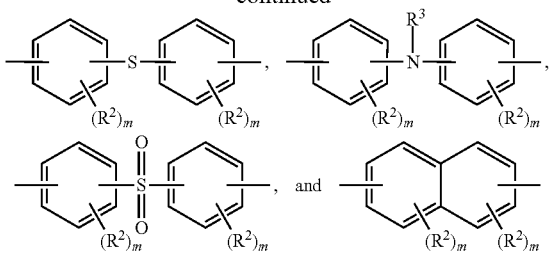

wherein each $R^2$ can be, independent of any other, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ alkoxyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, amino, hydroxyl, halide, or mixtures thereof, wherein any of the substituted groups named can be substituted with one or more of alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol groups;

$R^3$ can be H, substituted or unsubstituted $C_{1-20}$ alkyl, or substituted or unsubstituted $COC_{1-20}$ alkyl, wherein any of the substituted groups named can be substituted with one or more of alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol groups; and each m can be from 0 to 4, where an overlapping bond indicates that the bond can be at any carbon atom on the ring.

In specific examples, the heteroaryl containing moiety can be chosen from one or more of the following moieties:

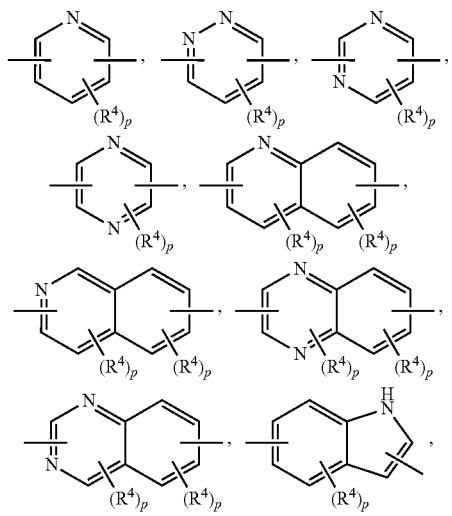

-continued

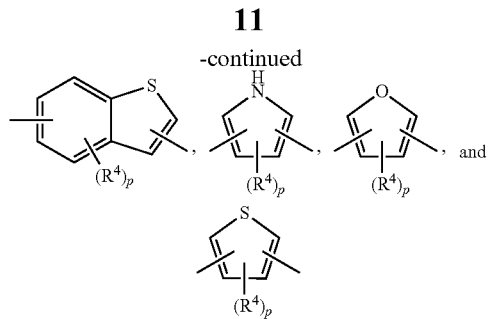

, and

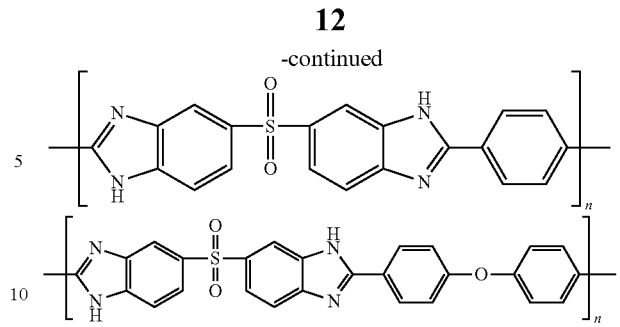

where n is from 2 to 200,000.

wherein
each $R^4$ can be, independent of any other, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ alkoxyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, amino, hydroxyl, halide, or mixtures thereof, wherein any of the substituted groups named can be substituted with one or more of alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol groups; and each p can be from 0 to 4, where an overlapping bond indicates that the bond can be at any carbon atom on the ring.

In specific examples, A can be an aryl containing moiety selected from the group consisting of:

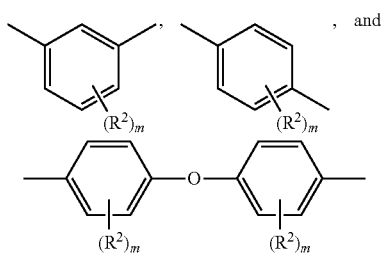

where $R^2$ and m are as defined above. In specific examples, m is 0.

In other specific examples, $R^1$ can be hydrogen. In other examples $R^1$ can be $C_{1-6}$ alkyl, $COC_{1-6}$ alkyl, $CO_2C_{1-6}$ alkyl, $C_{1-6}$ haloalkyl, $COC_{1-6}$ haloalkyl, $CO_2C_{1-6}$ haloalkyl, $CO_2C_{1-6}$ aryl, or $CO_2C_{1-6}$ alkylaryl.

In other examples, n can be from 2 to 100,000, from 2 to 10,000, from 2 to 1,000, from 1,000 to 200,000, from 1,000 to 100,000, from 1,000 to 10,000, from 10,000 to 200,000, from 10,000 to 100,000, or from 100,000 to 200,000.

Specific examples of polymers disclosed herein are:

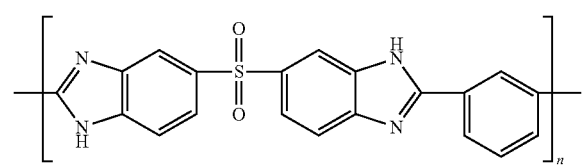

Due to the sulfonyl linkage between the two diaminophenyl groups, the disclosed polymers have a bent structure. The kinked structure introduced by the sulfonyl linkages in the PBI backbones is believed to reduce the chain packing efficiency and therefore enhance the gas transport properties of the PBIs. The disclosed polymers can have enhanced solubilities in dipolar aprotic solvents relative to polybenzimidazoles without sulfonyl moieties. Thermal gravimetric analysis shows that the disclosed polymers can be stable at elevated temperatures with 5% weight loss values of at least 485° C. in either air or $N_2$. Glass transition temperatures of three specific polymers disclosed herein were ascertained by dynamic mechanical analysis to be 438-480° C. These sulfonyl-containing polybenzimidazoles can have excellent gas separation properties for $H_2/CO_2$. Polymers from tetraaminodiphenylsulfone and either terephthalic or isophthalic acid crossed Robeson's upper bound for $H_2/CO_2$.

The disclosed polymers can be formed into thin films and/or applied onto a substrate.

Methods of Synthesis

The polybenzimidazoles with sulfonyl moieties disclosed herein can be prepared from 3,3',4,4'-tetraaminodiphenylsulfone.

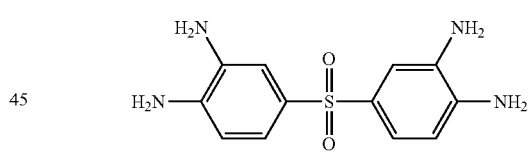

3,3',4,4'-tetraaminodiphenylsulfone (TADPS)

In the disclosed methods, TADPS can be contacted with a polycarboxylic acid (e.g., di-, tri-, tetracarboxylic acid, or dendrameric carboxylic acid), salt thereof, or activated ester thereof. In specific examples, TADPS can be contacted with an aryl or heteroaryl polycarboxylic acid, salt thereof, or activated ester thereof. In specific examples, TADPS can be contacted with an aryl or heteroaryl dicarboxylic acid, salt thereof, or activated ester thereof. This reaction can occur in the presence of Eaton's reagent, which is phosphorus pentoxide/methanesulfonic acid (PPMA). Eaton's reagent can be used as a condensation reagent in the presence of a solvent, or Eaton's reagent can be used as both a condensing agent and solvent. The amount of Eaton's reagent used should be in excess of the number of moles of TADPS.

In specific examples, the aryl dicarboxylic acid, salt thereof, or activated ester can be chosen from one or more of the following compounds:

13

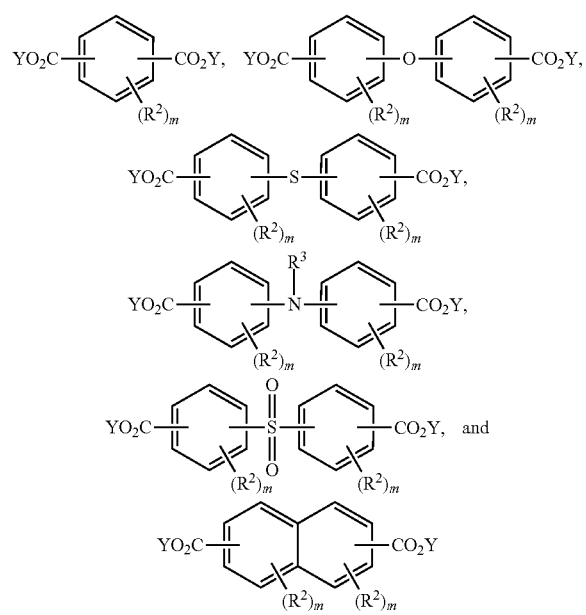

wherein each $R^2$ can be, independent of any other, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ alkoxyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, amino, hydroxyl, halide, or mixtures thereof, wherein any of the substituted groups named can be substituted with one or more of alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol groups;

$R^3$ can be H, substituted or unsubstituted $C_{1-20}$ alkyl, or substituted or unsubstituted $COC_{1-20}$ alkyl, wherein any of the substituted groups named can be substituted with one or more of alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol groups;

each m can be from 0 to 4; and each Y can be, independent of any other, H, Na, K, $NH_4$, succinimide, or carbodiimide, where an overlapping bond indicates that the bond can be at any carbon atom on the ring.

In specific examples, the heteroaryl dicarboxylic acid, salt thereof, or activated ester can be chosen from one or more of the following compounds:

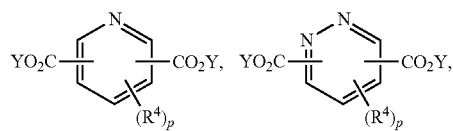

14

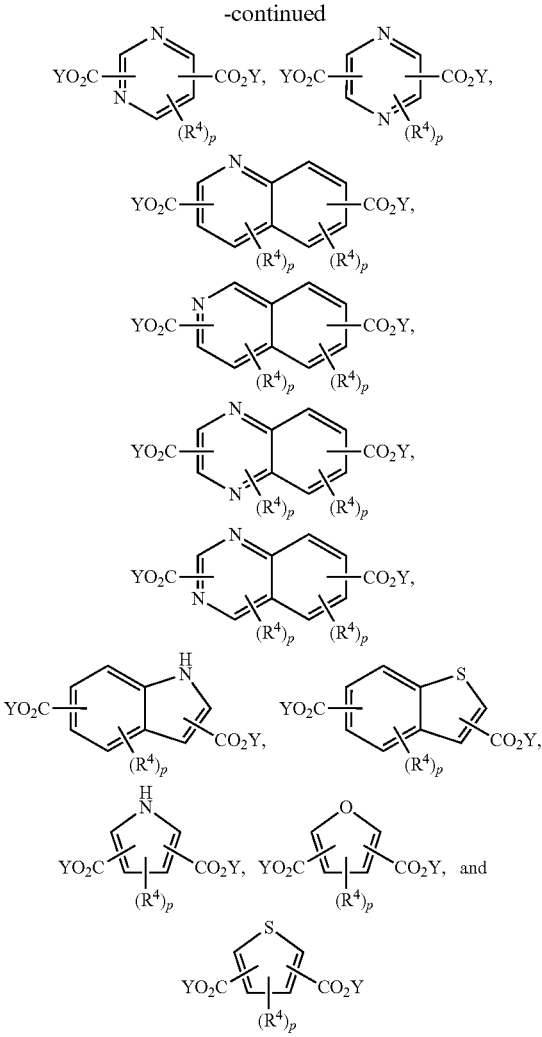

wherein each $R^4$ can be, independent of any other, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ alkoxyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, amino, hydroxyl, halide, or mixtures thereof, wherein any of the substituted groups named can be substituted with one or more of alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol groups;

each p can be from 0 to 4; and each Y can be H, Na, K, $NH_4$, succinimide, or carbodiimide, where an overlapping bond indicates that the bond can be at any carbon atom on the ring.

In specific examples, TADPS is reacted with can be an aryl dicarboxylic acid, chosen from one or more of the following:

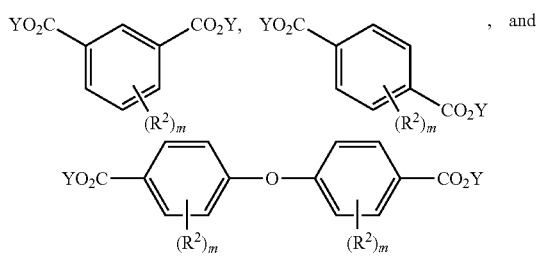

or a salt thereof, where $R^2$, Y, and m are as defined above. In specific examples, m is 0. In specific examples, Y is H.

In other specific examples, TADPS can be contacted with an aryl carboxylic acid chosen from isophthalic acid, terephthalic acid, naphthalene-1,2-dicarboxylic acid, naphthalene-1,3-dicarboxylic acid, naphthalene-1,4-dicarboxylic acid, naphthalene-1,5-dicarboxylic acid, naphthalene-1,6-dicarboxylic acid, naphthalene-1,7-dicarboxylic acid, naphthalene-1,8-dicarboxylic acid, naphthalene-2,3-dicarboxylic acid, naphthalene-2,6-dicarboxylic acid, naphthalene-2,7-dicarboxylic acid, 1,3,5-tricarboxylic benzoic acid, naphthalene-1,2,3-tricarboxylic acid, naphthalene-1,2,4-tricarboxylic acid, naphthalene-1,2,5-tricarboxylic acid, naphthalene-1,2,6-tricarboxylic acid, naphthalene-1,2,7-tricarboxylic acid, naphthalene-1,2,8-tricarboxylic acid, naphthalene-1,3,5-tricarboxylic acid, naphthalene-1,3,6-tricarboxylic acid, naphthalene-1,3,7-tricarboxylic acid, naphthalene-1,3,8-tricarboxylic acid, naphthalene-1,4,6-tricarboxylic acid, naphthalene-2,3,5-tricarboxylic acid, and naphthalene-2,3,6-tricarboxylic acid, and the like, salts thereof, activated esters thereof, and combinations thereof.

In further examples, the carboxylic acids can be converted to or obtained as their activated ester. For example, carboxylic acid groups can, depending on the conditions, be slow to react with a nucleophilic substituent on an active substance. However, these compounds can be converted into more reactive, activated esters by a carbodiimide coupling with a suitable alcohol, e.g., 4-sulfo-2,3,5,6-tetrafluorophenol, N-hydroxysuccinimide or N-hydroxysulfosuccinimide. This results in a more reactive activated ester moiety. Various other activating reagents that can be used for the polymerization reaction include, but are not limited to, 1-ethyl-3-(3-dimethylaminopropyl) carbodiimide (EDC), dicyclohexylcarbodiimide (DCC), N,N'-diisopropyl-carbodiimide (DIP), benzotriazol-1-yl-oxy-tris-(dimethylamino) phosphonium hexa-fluorophosphate (BOP), hydroxybenzotriazole (HOBt), and N-methylmorpholine (NMM), including mixtures thereof).

The temperature of the polycondensation reaction between TADPS and aryl or heteroaryl multicarboxylic acid, salt or activated ester thereof in the presence of Eaton's reagent can be less than 180° C. For example, the temperature of the polycondensation reaction can be less than 175° C., 170° C., 165° C., 160° C., 155° C., 150° C., 145° C., 140° C., or 135° C. In specific examples, the temperature of the polycondensation reaction can be from 135° C. to 145° C., from 135° C. to 140° C., or from 140 OC to 145° C.

After the reaction, the resulting polymers can be isolated and dried. They can also be cased into films or drawn into fibers.

The synthesis of the sulfonyl-containing tetraamine monomer, 3,3',4,4'-tetraaminodiphenylsulfone (TADPS), can be prepared from 4,4'-dichlorodiphenylsulfone, which is commercially available. The 4,4'-dichlorodiphenylsulfone can be contacted with a nitration reagent, to thereby provide a dinitrodichlorodiphenylsulfone; the dinitrodichlorodiphenylsulfone can be contacted with an amination reagent, to thereby provide dinitrodiaminodiphenylsulfone; and the dinitrodiaminodiphenylsulfone can be reduced with a reducing reagent, to thereby provide tetraaminodiphenylsulfone.

The expression "nitration reagent" refers to a reagent or a mixture of reagents that can add a nitro group to an aryl by electrophilic substitution. Examples of nitration reagents include nitric acid, a mixture of nitric acid and sulfuric acid ($HNO_3/H_2SO_4$), a mixture of one or more of $NaNO_3$, $NaNO_3$ or $CuNO_3$ with one or more acids selected from hydrochloric acid, hydrobromic acid, sulfuric acid, and nitric acid, a mixture of $NaNO_2$ and acetic acid, $N_2O_5/P_2O_5/CCl_4$, HONO, $EtONO_2$, $CH_3COONO_2$, $NO_2$ with $CF_3SO_3$, and Vanadium(v) oxytrinitrate ($VO(NO_3)_3$).

The nitration reaction can occur at a temperature of from 0 to 50° C., for example at from 5° C., 10° C., 15° C., 20° C., 25° C., 30° C., 35° C., 40° C., 45° C., or 50° C., where any of the stated values can form an upper or lower endpoint of a range. In a specific example, the temperature of the nitration reaction can be 25° C. The nitration reaction can occur at a atmospheric pressure.

The expression "amination reagent" refers to a reagent or a mixture of reagents that can add an amine group to an aryl by nucleophilic substitution. Examples of amination reagents include ammonium hydroxide, ammonium carbonate, ammonium bicarbonate, ammonium phosphate, and O-mesitylenesulfonylhydroxylamine.

The amination reaction can occur at a temperature of from room temperature to 160° C., though higher temperatures can be used. For example, the temperature of the polycondensation reaction can be 20° C., 30° C., 40° C., 50° C., 60° C., 70° C., 80° C., 90° C., 100° C., 110° C., 120° C., 125° C., 130° C., 135° C., 140° C., 145° C., 150° C., 155° C., or 160° C., where any of the stated values can form an upper or lower endpoint of a range. In a specific example, the temperature of the amination reaction can be from 120° C. to 160° C., or more specifically at 140° C. The amination reaction can occur at ambient or elevated pressure, for example at 30, 40, 50, 60, 70, 80, 90, or 100 psi, where any of the stated values can form an upper or lower endpoint of a range. In a specific example, the pressure of the amination reaction can be 60 psi.

The expression "reducing reagent" refers to a reagent or a mixture of reagents that can reduce a nitroaryl to an aryl amine. Examples of reducing reagents include hydrogen with palladium catalyst (e.g., palladium on carbon, palladium (II) acetate, allylpalladium(II) chloride dimer, di-µ-chlorobis[(1,2,3-η)-1-phenyl-2-propenyl]dipalladium(II), cyclopentadienyl(allyl)palladium(II), cyclopentadienyl[(1,2,3-n)-1-phenyl-2-propenyl]palladium(II), palladium(II) chloride, palladium(II) pivlate, palladium(0)dba2, palladium (II) acetylacetonate, tetrakis(triphenylphosphine)palladium (0)), hydrogen with Rainey nickel catalyst, lithium aluminum hydride, diisobutylaluminum hydride, and sodium borohydride.

The reduction reaction can occur at a temperature of from 50° C. to 150° C. For example, the temperature of the polycondensation reaction can be 50° C., 60° C., 70° C., 80° C., 90° C., 100° C., 110° C., 120° C., 130° C., 140° C., or 150° C., where any of the stated values can form an upper or lower endpoint of a range. In a specific example, the temperature of the amination reaction can be 100° C.

Methods of Use

The polymers disclosed herein can be used to reduce target gases from a stream. Described herein is a method for reducing a target gas from a stream, comprising contacting the stream with a polymer as described herein. The target gases present in the stream can absorb and/or dissolve into the polymer. The target gases present in the stream can be reduced from the stream and increased in or on the polymer. The polymer and the stream can then be separated. The stream will have a reduced amount of target gas and the polymer will have an increased amount of target gas.

The stream can be a liquid stream, including, for example, a solvent where a chemical reaction is taking place, or a gaseous stream, including, for example, natural gas stream or a flue gas stream.

Examples of target gases include $CO_2$, CO, COS, $H_2S$, $SO_2$, NO, $N_2O$, mercaptans, $H_2O$, $O_2$, $H_2$, $N_2$, $Cl_2$, volatile organic compounds, and mixtures of these. In some examples, the target gas is selected from the group consisting of $CO_2$ and $H_2$.

The method for reducing target gases from a stream can include contacting the stream with a polymer as described herein. For example, target gases from a gas stream (e.g., a natural gas stream or a flue gas stream) can be reduced according to this method.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

4,4'-Dichlorodiphenylsulfone (DCDPS) was kindly provided by Solvay and recrystallized from toluene before use. Isopropanol, acetic acid, ammonium hydroxide solution (29%), nitric acid (69.3%) and sulfuric acid were purchased from Spectrum Chemicals and used as received. Hydrazine hydrate, palladium on carbon, sodium bicarbonate and 4,4'-oxybis(benzoic acid) were purchased from Sigma-Aldrich and used as received. Dimethylsulfoxide (DMSO), dimethylacetamide (DMAc) and N-methyl-2-pyrrolidone (NMP) were purchased from Fisher and used as received. Eaton's Reagent was purchased from Alfa Aesar. Celite was purchased from EMD Chemicals. Isophthalic acid was provided by Amoco and recrystallized from methanol before use. Terephthalic acid was provided by Eastman and recrystallized from methanol before use.

$^1$H NMR analysis was performed on a Varian Inova spectrometer operating at 400 MHz. All spectra were obtained from 15% (w/v) 1-mL solutions in DMSO-$d_6$.

Synthesis of 3,3',4,4'-tetraaminodiphenylsulfone Monomer (TADPS)

Figure 2:
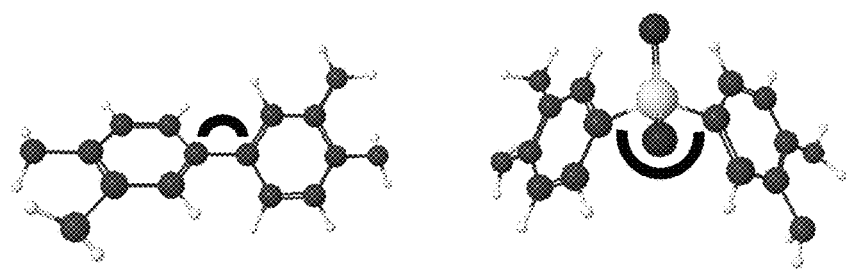
FIG. 2 shows the structure of 3,3'-diaminobenzidine (left) vs TADPS (right).

A synthesis procedure for the TADPS monomer has been previously reported as a four-step method starting from 4,4'-diaminodiphenylsulfone (DDS) (Lakshmi Narayan T V., et al., Polybenzimidazoles. VI. Polybenzimidazoles Containing Aryl Sulfone Linkages. *J Polym Sci Part A-1 Polym Chem* 1967; 5:1113-8). In this route, protection and deprotection of the amino groups from DDS were required before and after nitration. As a result, synthesis of TADPS via this method has more synthetic steps, which contributes to inefficiency and increased cost. A three-step synthetic route was developed herein to make polymer-grade TADPS monomer starting with dichlorodiphenylsulfone (DCDPS), which is a widely used monomer for polysulfone synthesis (FIG. 1). Nitration of DCDPS was conducted first to activate the sites with the chlorine substituents toward amination by nucleophilic substitution with ammonium hydroxide. Finally TADPS was achieved by reducing the nitro groups to amines. This method also produced an overall yield of 57% which is higher than the reported yield (34%) of TADPS derived from DDS (Id.). The $SO_2$ linkage provides a bend in the structure to increase solubility of the PBIs (FIG. 2).

Synthesis of 3,3'-dinitro-4,4'-dichlorodiphenylsulfone

Excess 4,4'-dichlorodiphenylsulfone (100.5 mmol, 28.75 g) and 290 mL of 96% $H_2SO_4$ were added to a 500-mL three-necked flask equipped with a condenser, mechanical stirrer and addition funnel. The reaction mixture was stirred at room temperature until the 4,4'-dichlorodiphenylsulfone completely dissolved. Nitric acid (69.3%) (201.0 mmol, 18.28 g) was added dropwise via the addition funnel. Upon completion of addition, the solution was stirred for 6 h at room temperature. The final heterogeneous solution containing a pale yellow precipitant was poured into 2 L of deionized water, and $NaHCO_3$ was added until the solution reached a pH of 7. Then the crude product was filtered and dried in vacuo at 100° C. The product was recrystallized from acetic acid to obtain a 92% yield. $^1$H NMR ($d_6$-DMSO): δ8.70 (d, 2H), δ 8.32 (d, 2H), δ 8.29 (dd, 2H), δ 8.05 (d, 2H).

Synthesis of 3,3'-dinitro-4,4'-diaminodiphenylsulfone 3,3'-Dinitro-4,4'-dichlorodiphenylsulfone (125.1 mmol, 21.80 g), $NH_4OH$ (312.7 mmol, 43.6 mL) and 300 mL of DMSO were added into a 500-mL pressure reactor equipped with heating coils and an overhead stirrer. The reactor was pressurized to 60 psi with nitrogen then heated to 140° C. After 16 h, the reaction mixture was cooled and precipitated in deionized water. The yellow precipitant was filtered, washed with copious amounts of water and dried in vacuo at 80° C. A 90% yield of product was obtained. $^1$H NMR ($d_6$-DMSO): δ8.42 (d, 2H), δ 8.04 (bs, 4H), δ 7.75 (dd, 2H), δ 7.10 (d, 2H).

Synthesis of 3,3',4,4'-tetraaminodiphenylsulfone 3,3'-Dinitro-4,4'-diaminodiphenylsulfone (30.9 mmol, 10.46 g), 1.05 g Pd/C and 700 mL of isopropanol were added to a 1000-mL three-necked flask equipped with a condenser, mechanical stirrer, and addition funnel. The reaction mixture was heated in a thermocouple-regulated oil bath set at 100° C. and stirred. Hydrazine hydrate (10.2 mL, 216.4 mmol) was added dropwise through the addition funnel. After complete addition, the solution was stirred and refluxed for 12 h in the 100° C. oil bath. The reaction mixture was hot-filtered through Celite. The product started to crystallize from the filtrate upon cooling. The light grey lustrous crystals were filtered and washed with water. The monomer product was dried in vacuo at 100° C. overnight to afford a 62% yield. Melting point: 176° C.

Figure 3:
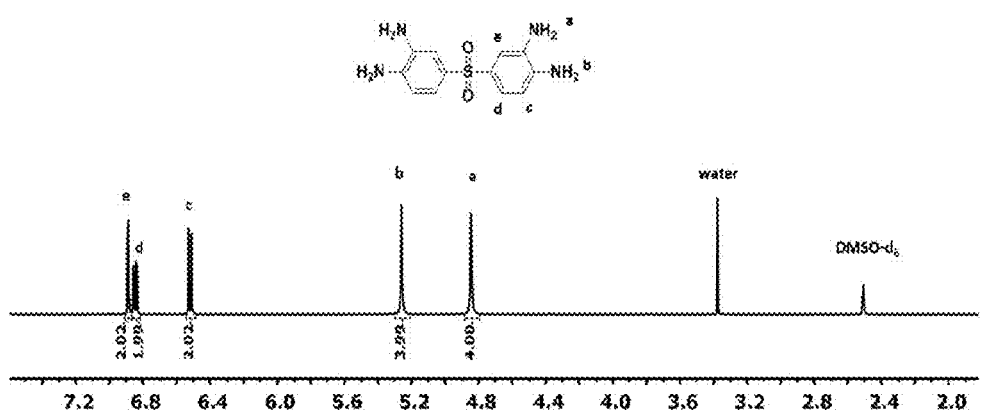
FIG. 3 shows the $^1$H-NMR spectrum of the TADPS monomer.

The $^1$H NMR spectrum of TADPS is shown in FIG. 3. All of the peaks integrate appropriately to confirm the molecular structure. The $^1$H NMR spectrum was also free of "extra" peaks that would correspond to organic side products or contaminants. The melting point of the recrystallized product was in good agreement with the reported value (Id.).

Synthesis of Tetraaminodiphenylsulfone-Isophthalic Acid Polybenzimidazole (TADPS-IPA), Tetraaminodiphenylsulfone-Terephthalic Acid Polybenzimidazole (TADPS-TPA), and Tetraaminodiphenylsulfone-Oxybis(Benzoic Acid) Polybenzimidazole (TADPS-OBA)

Figure 4:
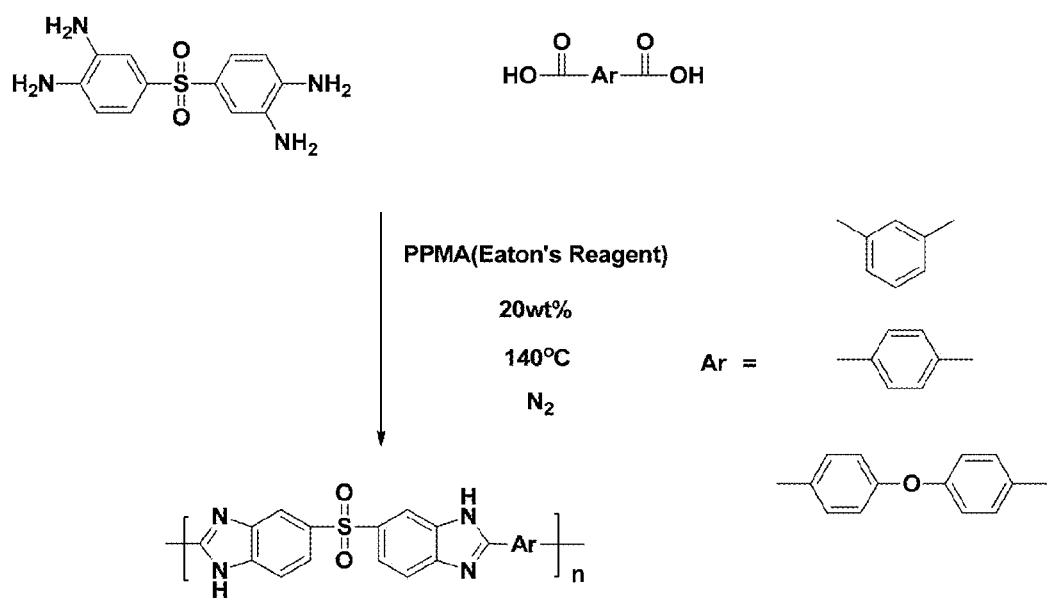
FIG. 4 shows the synthesis of polybenzimidazole using Eaton's reagent as a solvent.

The TADPS-based PBIs disclosed herein were synthesized by direct polycondensation using Eaton's reagent as both a solvent and condensing agent (FIG. 4) (Ueda et al., *Macromolecules* 1985; 18:2723-6). PBI synthesis in acid solution was originally carried out in poly(phosphoric acid) (PPA), which is a beneficial method for preparing acid-doped PBI fuel cell membranes (Mader J A, et al., Sulfonated Polybenzimidazoles for High Temperature PEM Fuel Cells. *Macromolecules* 2010; 43:6706-15). However, using Eaton's reagent as a reaction solvent has advantages for general PBI synthesis. First, Eaton's reagent is much less viscous than PPA and thus it is easier to handle. Secondly, the method conducted in Eaton's reagent can be accomplished at a lower temperature (135-145° C.) than that required in PPA (180-200° C.). Finally, Eaton's reagent is easier to remove than PPA once the polymerization is completed (Jouanneau J, et al., Synthesis of Sulfonated Polybenzimidazoles from Functionalized Monomers: Preparation of Ionic Conducting Membranes. *Macromolecules* 2007; 40:983-90).

The TADPS-IPA polymer was synthesized by direct polycondensation of the tetraamine and dicarboxylic acid in Eaton's reagent (phosphorus pentoxide/methanesulfonic acid, PPMA) which served as both a condensing agent and solvent. Specifically, TADPS (11.6 mmol, 3.2200 g), IPA (11.6 mmol, 1.9220 g) and Eaton's reagent (22 mL) were added to a 100-mL three-necked flask equipped with a mechanical stirrer, nitrogen inlet, and a condenser. A stirred, thermocouple-regulated oil bath was used to heat the reaction to 145° C. After refluxing for 24 h, the hot viscous solution was poured into 1 L of a stirring saturated NaHCO$_3$ solution to precipitate a highly fibrous solid. The solid was filtered again on an aspirator and then boiled in 500 mL of deionized water for 2 h (repeated 4 times with new DI water each time) to remove any residual salts. The solid polymer was finally dried at 150° C. in vacuo for 24 h. Yield was 95%.

The TADPS-TPA and TADPS-OBA polymers were synthesized in the exact manner as the TADPS-IPA polymer, except TPA (11.6 mmol, 3.2200 g) or OBA (11.6 mmol, 2.9854 g) were used instead of IPA. Yields were 96 and 95% respectively.

Figure 5:
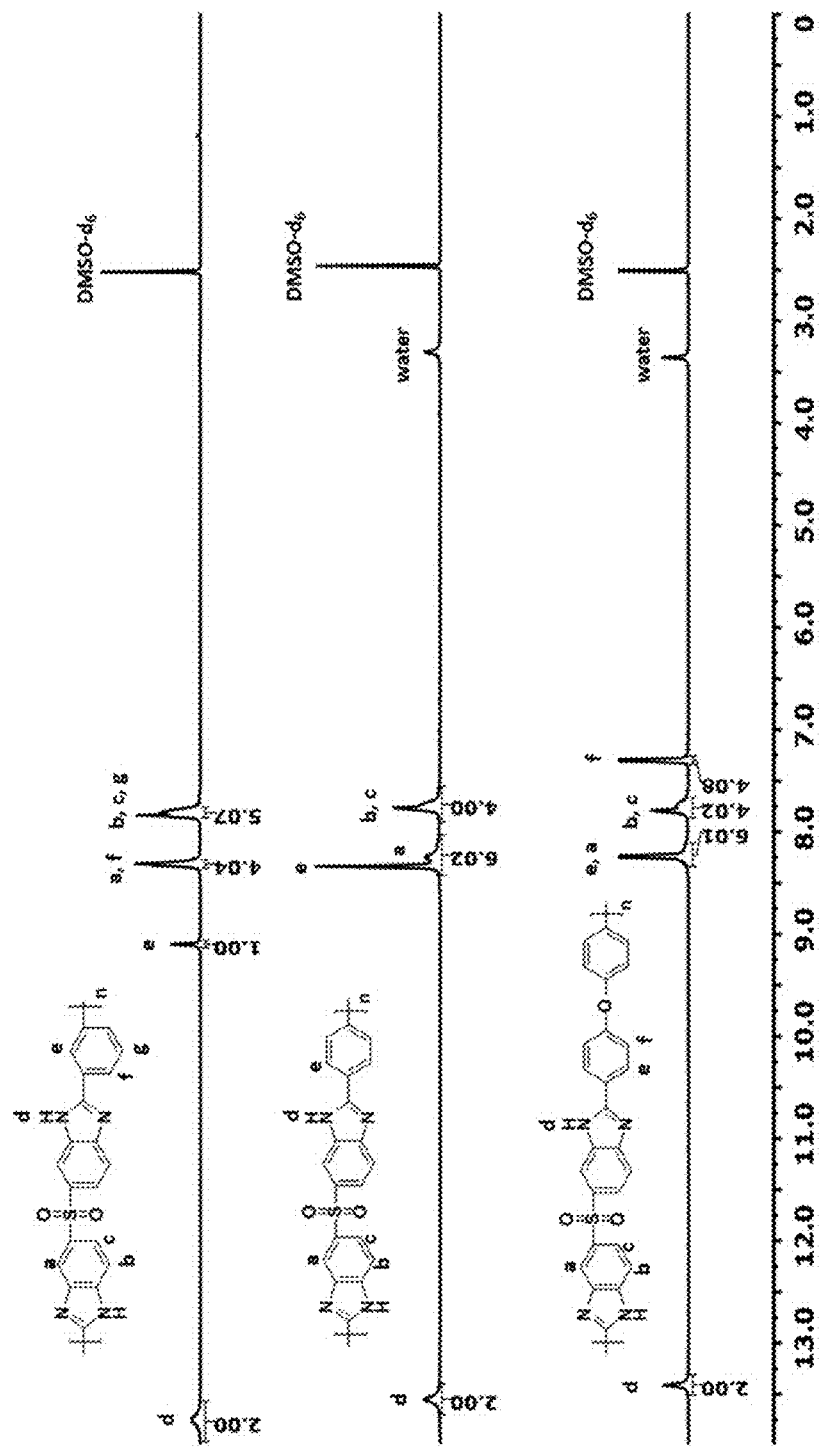
FIG. 5 shows the $^1$H-NMR spectra of TADPS-based polybenzimidazoles.

After polymer isolation and drying, the TADPS-based PBIs were characterized by NMR spectroscopy. The $^1$H NMR spectra shown in FIG. 5 confirm the expected polymer structures and show that the solvent was effectively removed. The integral values were consistent with the expected chemical structures and no extraneous peaks were observed in the spectra.

Size Exclusion Chromatography

Size exclusion chromatography (SEC) was conducted on the TADPS-IPA, TADPS-TPA and TADPS-OBA polybenzimidazoles to measure molecular weight distributions. The solvent was DMAc that was distilled from CaH$_2$ and that contained dry LiCl (0.1 M). The column set consisted of 3 Agilent PLgel 10-μm Mixed B-LS columns 300×7.5 mm (polystyrene/divinylbenzene) connected in series with a guard column having the same stationary phase. The column set was maintained at 50° C. An isocratic pump (Agilent 1260 infinity, Agilent Technologies) with an online degasser (Agilent 1260), autosampler and column oven was used for mobile phase delivery and sample injection. A system of multiple detectors connected in series was used for the analyses. A multi-angle laser light scattering (MALLS) detector (DAWN-HELEOS II, Wyatt Technology Corp.), operating at a wavelength of 658 nm, a viscometer detector (Viscostar, Wyatt Technology Corp.), and a refractive index detector operating at a wavelength of 658 nm (Optilab T-rEX, Wyatt Technology Corp.) provided online results. The system was corrected for interdetector delay and band broadening. Data acquisition and analysis were conducted using Astra 6 software from Wyatt Technology Corp. Validation of the system was performed by monitoring the molar mass of a known molecular weight polystyrene sample by light scattering. The accepted variance of the 21,000 g/mole polystyrene standard was defined as 2 standard deviations (11.5% for $M_n$ and 9% for $M_w$) derived from a set of 34 runs.

Figure 6:
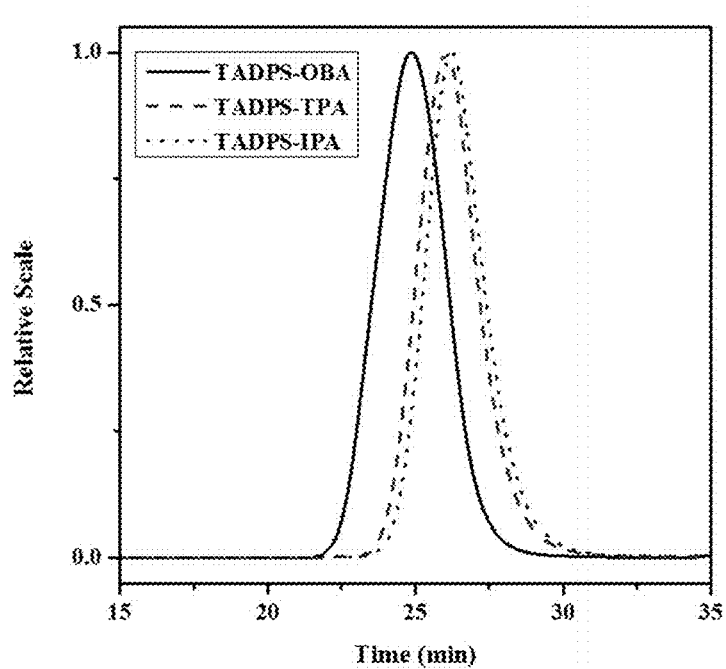
FIG. 6 shows the light scattering SEC chromatograms of TADPS-based polybenzimidazoles.

The TADPS-based PBIs were sufficiently high molecular weight to form transparent and ductile films. SEC of the PBIs quantitatively substantiated the molecular weights (FIG. 6 and Table 1). The chromatograms of the polymers showed a monomodal Gaussian distribution with reasonable polydispersities. It is noted that the polydispersities in Table 1 are somewhat lower than the value of two that is expected for polymers prepared by polycondensation. The reported molecular weights were measured by static light scattering in the SEC which directly measures weight average molecular weight. Thus, the $M_w$ values may be more accurate than the $M_n$ values that were calculated from the software.

TABLE 1

Molecular weights of TADPS-based polybenzimidazoles by SEC

|  | $M_n$ (kDa) | $M_w$ (kDa) | PDI | dn/dc (mL/g) |
| --- | --- | --- | --- | --- |
| TADPS-TPA | 20 | 31 | 1.5 | 0.31 |
| TADPS-IPA | 18 | 29 | 1.6 | 0.28 |
| TADPS-OBA | 35 | 63 | 1.8 | 0.30 |

Membrane Preparation

For each polymer, 0.5 g of polymer was weighed into a scintillation vial, 10 mL of DMAc was added, and the mixture was stirred until a homogeneous solution was obtained. The solution was syringe-filtered through a 0.45 μm PTFE filter into a new vial. Each vial was sonicated for 30 min to remove dissolved gases. A 10×10 cm$^2$ glass plate was cleaned with acetone and dried before use. The solution was cast on the glass plate on a leveled casting surface in the vacuum oven and allowed to dry under full vacuum at room temperature overnight. The temperature was then increased to 60° C. under full vacuum for 4 h. The temperature was increased to 100° C. for another 1 h under full vacuum. The film was removed from the glass plate with the aid of water and treated in boiling water for 4 h to remove remaining solvent. The following day the film was dried in the oven at 140° C. under full vacuum.

Solubility and Water Uptake

Solubilities of the PBIs were determined by stirring 0.5 grams of polymer powder in 10 mL of solvent for 24 h at room temperature or 100° C. The solvents were NMP, DMAc, DMSO and THF.

The membrane water uptake was determined by the weight difference between dry and wet membranes. Membranes (~0.2 grams) that had been vacuum-dried at 120° C. for 24 h were weighed ($W_{dry}$) and then immersed in deionized water at room temperature for 24 h. The wet membrane was blotted dry and immediately weighed again ($W_{wet}$). The water uptake of the membranes was calculated according to Equation 1. The water uptake measurements of the membranes were carried out in triplicate independently with different pieces of membranes to check the reproducibility of the results.

$$\text{Water Uptake (\%)} = \frac{W_{wet} - W_{dry}}{W_{wet}} \times 100 \quad (1)$$

The low solubility of PBIs often limits their processibility by solvent-casting to form thin membranes. The solubilities in various solvents and water uptake of these PBIs are listed in Table 2. With introduction of sulfonyl linkages into the PBI chains, their solubilities were significantly enhanced compared to poly-[2,2'-(m-phenylene)-5,5'-bisbenzimidazole], the commercial polybenzimidazole (CELAZOLE™, m-PBI). All three of the TADPS-based PBIs were completely soluble in common dipolar aprotic solvents at a 5.0 wt % polymer concentration, which is in the range of concentrations for solution processing to form thin membranes. All of these polymers were still insoluble in common organic solvents such as THF and methanol.

PBIs, in general, have high water uptake due to the hydrophilicity of the imidazole ring (Brooks N W, et al., An NMR study of absorbed water in polybenzimidazole. *Polymer* 1993; 34:4038-42). All of these sulfonyl-containing PBIs exhibited high hydrophilicity, with TADPS-TPA showing a water uptake of 25 wt %.

TABLE 2

Solubility in common solvents at 25° C. and water uptake of polybenzimidazoles.

| | NMP | DMAc | DMSO | THF | Water Uptake |
|---|---|---|---|---|---|
| TADPS-IPA | ++ | ++ | ++ | − | 18% |
| TADPS-TPA | + | ++ | ++ | − | 25% |
| TADPS-OBA | ++ | ++ | ++ | − | 12% |
| m-PBI* | + | + | ++ | − | 15% |

Soluble at room temperature (++), partially soluble at room temperature and fully soluble at refluxing temperature (+), and insoluble (−).
*The data for m-PBI (CELAZOLE ™) is from previous literature (Id.; Klaehn J R, et al., New Soluble N-Substituted Polybenzimidazoles by Post-Polymerization Modification. *Polym Prepr* 2005; 46: 708-9). [22, 21]

X-Ray Diffraction

Powder X-ray diffraction (PXRD) was performed using a Scintag X-1 theta-theta diffractometer, with a Cu X-ray source and a Si(Li) solid state detector tuned to Cu Kα radiation of 1.54 Å wavelength to characterize the amorphous nature of the PBIs in this study.

Figure 7:
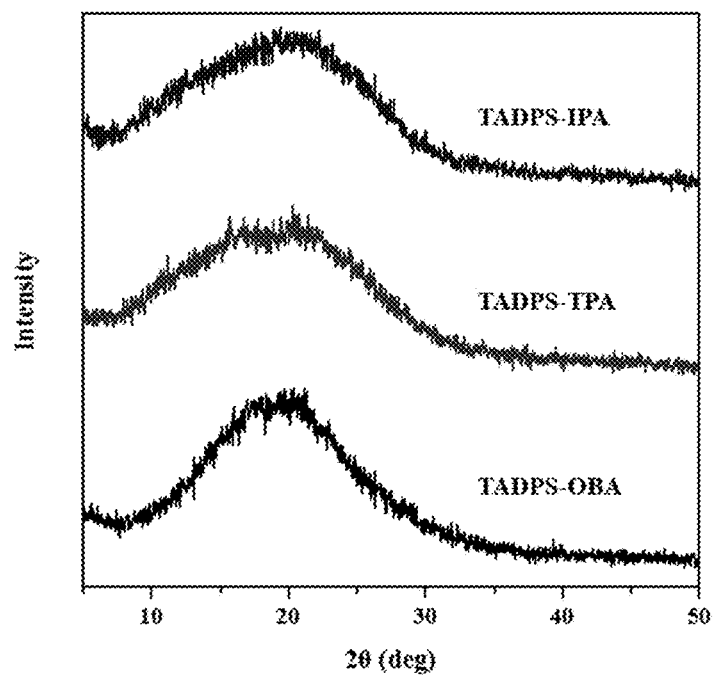
FIG. 7 shows the XRD of TADPS-based polybenzimidazoles.

XRD was used to probe whether any regions of crystallinity existed in these sulfonyl-containing PBI membranes. As shown in FIG. 7, the broad amorphous halos observed for all three of the polymers confirmed that they were completely amorphous. This can be desirable for gas separation membranes since crystalline domains reduce both gas diffusivity and solubility resulting in a reduction in permeability (Ghosal K, et al., Gas Separation Using Polymer Membranes: An Overview. *Polym Adv Technologies* 1994; 5:673-97).

Thermogravimetric Analysis and Dynamic Mechanical Analysis

The TADPS-based PBIs were characterized by thermogravimetric analysis (TGA) and dynamic mechanical analysis (DMA). TGA scans were conducted using a TA Instruments Q5000 thermogravimetric analyzer under nitrogen and air atmospheres. A heating rate of 10° C. min$^{-1}$ was employed from 25 to 700° C. Dynamic mechanical analysis was performed using a TA Instruments Q800 configured in tensile geometry. Storage modulus (E') and tan δ were measured in a temperature sweep mode (1 Hz, 2° C. min$^{-1}$) at temperatures ranging from 150 to 550° C. under a N$_2$ atmosphere.

Figure 8A:
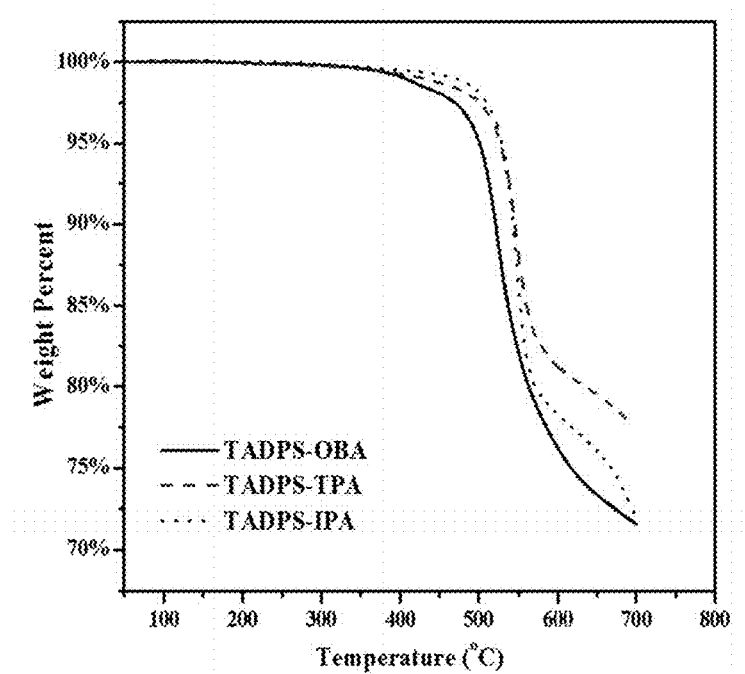
FIG. 8A shows the thermal gravimetric analysis of sulfone-containing polybenzimidazoles in $N_2$.
Figure 8B:
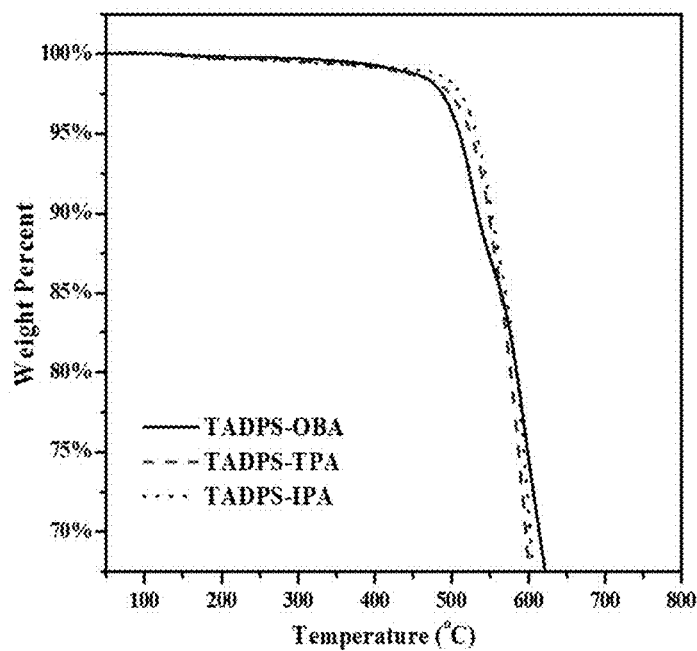
FIG. 8B shows the thermal gravimetric analysis of sulfone-containing polybenzimidazoles in air.

PBIs are renowned for their excellent thermal stability (Vogel et al., *J Polym Sci* 1961; 50:511-39; Berchtold et al., *J Membr Sci* 2012; 415-416:265-70). Introduction of the SO$_2$ linkage into the polymer chain resulted in polymers that did not show any weight loss before 400° C. in either air or N$_2$ (FIGS. 8A and 8B). The 5% weight loss temperatures are listed in Table 3. It was observed that all of the TADPS-based PBIs exhibited lower decomposition temperatures than m-PBI, and this was likely due to the introduction of the relatively less stable sulfonyl groups. Overall, the high thermal stabilities of all three TADPS-based PBIs make them potential candidates for high temperature membrane separations.

TABLE 3

Thermal properties of polybenzimidazoles

| | $T_g$ | 5% weight loss in N$_2$ | 5% weight loss in Air |
|---|---|---|---|
| TADPS-OBA | 428° C. | 485° C. | 510° C. |
| TADPS-TPA | 480° C. | 499° C. | 525° C. |
| TADPS-IPA | 447° C. | 503° C. | 532° C. |
| m-PBI* | 417° C. | 576° C. | — |

*The reported data for m-PBI (CELAZOLE ™) is from previous literature (Menczel J. Thermal Measurements on Poly[2,2'-(m-phenylene)-5,5'-bibenzimidazole] Fibers. *J Therm Anal Calorim* 2000; 59: 1023-7).

Figure 9A:
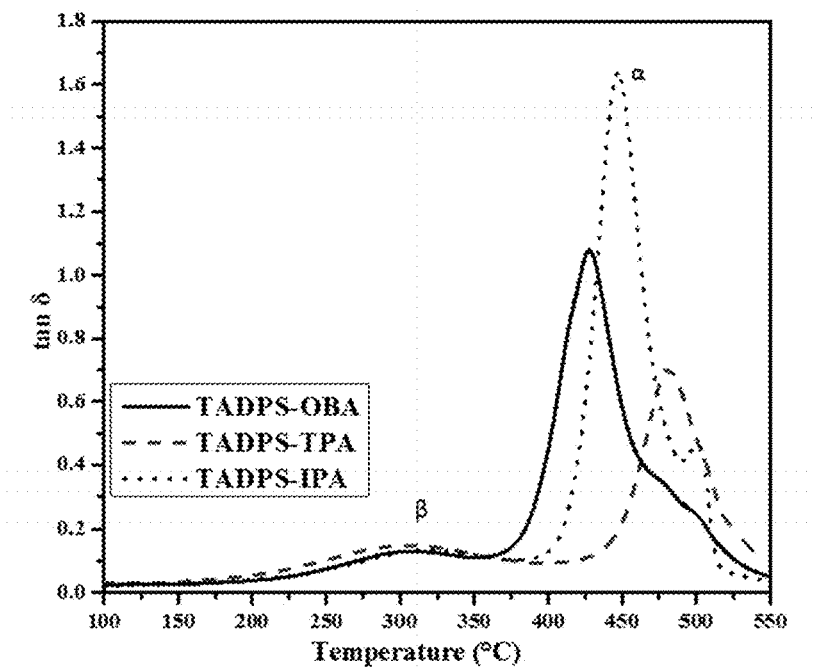
FIG. 9A shows the dynamic mechanical analysis (tan δ vs temperature) of TADPS-based polybenzimidazoles under $N_2$.
Figure 9B:
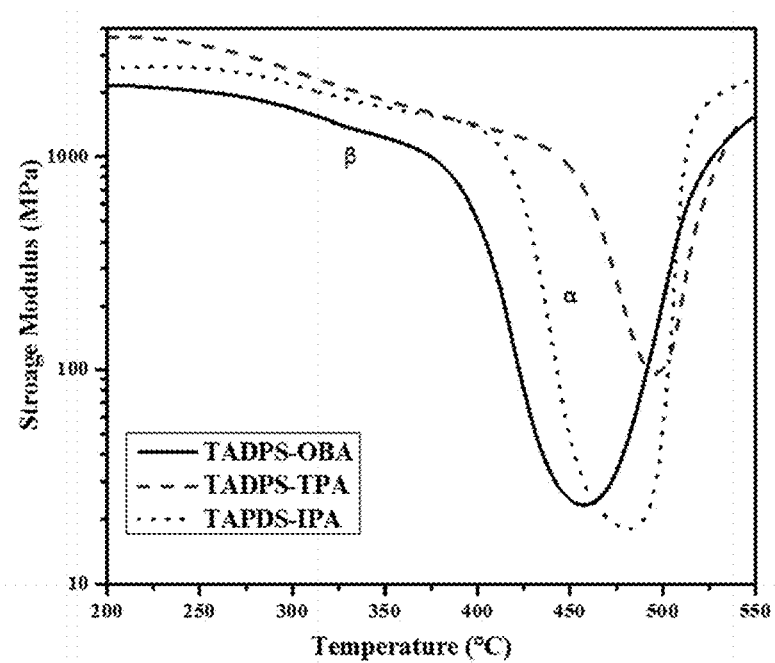
FIG. 9B shows the dynamic mechanical analysis (storage modulus vs temperature) under $N_2$.

DMA results for the series of TADPS-based PBIs under N$_2$ are shown in FIGS. 9A and 9B. These samples were treated with boiling water for 4 hours and then dried in vacuo at 180° C. for at least 24 hours before DMA testing. Two motional relaxation processes were observed with increasing temperature (designated β and α), consistent with results reported for other PBIs such as m-PBI (Id.). Here, the β processes correspond to localized sub-glass transition motions of limited range, while the α-process corresponds to the glass-rubber relaxation.

Storage moduli (FIG. 9B) reveal that all three of these sulfonyl-containing PBIs maintain a stable plateau up to at least 230° C. Up to this temperature, TADPS-TPA, TADPS-IPA and TADPS-OBA maintain a storage modulus of 3.5, 2.6 and 2.1 GPa, respectively. Above that temperature, the storage moduli of these PBIs started to decrease slowly as the temperature was increased up to 430, 397, and 371° C. respectively. The initial reductions in storage moduli corresponded to the beta relaxations of these polymers (Id.). Afterwards, a large drop in storage modulus was observed for all three of the polymers which corresponds to the glass transition. The storage modulus curves indicated that the TADPS-based PBIs are high-temperature amorphous polymers that maintain their structural stiffness up to 430, 397, and 371° C. respectively. For all three of these materials, at temperatures beyond 496, 481, and 456° C. respectively (very close to the 5% weight loss values in $N_2$ from TGA), a stiffening occurs that is likely associated with degradation by in-situ crosslinking.

In comparison with m-PBI, the three TADPS-based PBIs had higher glass transition temperatures, which is likely due to the enhanced rigidity imparted by the double bond feature of the C—S linkage (Guo R, et al., Aromatic Polyethers, Polyetherketones, Polysulfides, and Polysulfones. In: Matyjaszewski K, Möller M, editors. *Polym Sci Compr Ref*, vol. 5, Elsevier B. V.; 2012, p. 377-430). Similar glass transition temperature enhancements in polymers have been observed with comparisons between poly(arylene ether) and poly (arylene ether sulfone) (Robeson et al., *Appl Polym Symp* 1975; 26:375-85). The TADPS-OBA PBI had a lower glass transition temperature than the other two polymers. This can be attributed to the flexible ether linkages in the TADPS-OBA PBI that reduces the rigidity of the polymer chain.

Gas Transport

Pure gas permeabilities of $H_2$, He, $O_2$ and $CO_2$ (UHP grade, Airgas, Radnor, Pa., USA) through the TADPS-based PBIs were measured via a constant-volume, variable-pressure method (Lin H, et al., Permeation and Diffusion. In: Czichos H, Smith L, Saito T, editors. Springer-handb. *Mater Meas Methods*, Springer; 2006, p. 371-87). The upstream pressure was measured by a Honeywell Super TJE transducer (Honeywell Sensotec, Columbus, Ohio, USA) with a 1500 psig range. The downstream pressure was maintained under vacuum and measured by an MKS Baratron 626B (MKS Instruments, Andover, Mass., USA). Coupons of each film were masked to a metal disk with a pre-machined hole using Master Bond EP46HT-2 epoxy (Master Bond Inc., Hackensack, N.J., USA), and the exposed film area was measured. Prepared samples were stored in a desiccator prior to placement in the pressure cell to reduce exposure to moisture. Mounted membrane samples were placed in a 47-mm high-pressure filter holder (Millipore, Billerica, Mass., USA) and degassed at 35° C. overnight. The downstream pressure rise was measured over a range of upstream pressures, and the calculated permeabilities are reported herein at 10 atm and 35° C.

Tables 4-5 show the permeabilities ($H_2$, He, $O_2$ and $CO_2$) and ideal selectivities of the three sulfonyl-containing PBIs at 35° C. The permeability coefficients for TADPS-OBA were higher than those of TADPS-IPA and TADPS-TPA and increased from TADPS-IPA to TADPS-TPA to TADPS-OBA. For example, permeability of $CO_2$ was 0.11 Barrer for TADPS-IPA, 0.28 Barrer for TADPS-IPA, and 0.56 Barrer for TADPS-OBA. The ether linkages in TADPS-OBA introduce additional kinks in the polymer backbone that disrupt chain packing, leading to higher gas permeability coefficients relative to those for the TADPS-TPA and TADPS-IPA polymers. This same phenomenon has also been observed for aromatic polyimides (Tanaka K, et al., Permeability and permselectivity of gases in fluorinated polyimides. *Polymer* 1992; 33:585-92; Tanaka K, et al., Effect of Methyl Substituents on Permeability and Permselectivity of Gases in Polyimides Prepared from Methyl-Substituted Phynylenediamines. *J Polym Sci Part B Polym Phys* 1992; 30:907-14). Permeability measurements of slower gases ($N_2$, $CH_4$) were attempted, but the estimated permeabilities were below the detection limit of the instrument.

TABLE 4

Permeabilities for TADPS-based polybenzimidazoles tested at 35° C. and 10 atm

| Samples | Thickness (μm) | Pure Gas Permeabilities (Barrer) | | | |
|---|---|---|---|---|---|
| | | $H_2$ | He | $O_2$ | $CO_2$ |
| TADPS-OBA | 19.4 ± 0.7 | 5.7 ± 0.2 | 6.7 ± 0.2 | 0.17 ± 0.01 | 0.56 ± 0.02 |
| TADPS-TPA | 19.5 ± 1.1 | 5.5 ± 0.3 | 6.7 ± 0.4 | 0.09 ± 0.01 | 0.28 ± 0.02 |
| TADPS-IPA | 21.5 ± 1.7 | 3.6 ± 0.3 | 5.1 ± 0.4 | 0.05 ± 0.04 | 0.11 ± 0.01 |

The TADPS-IPA and TADPS-TPA PBIs are meta- and para-linked isomers. Generally, para-linked linear aromatic polymers pack less efficiently and have more segmental mobility than meta-oriented aromatic polymers (Mi Y, et al., Dependence of the gas permeability of some polyimide isomers on their intrasegmental mobility. *J Membr Sci* 1993; 77:41-8). Thus, higher fractional free volumes and higher permeabilities for para-oriented aromatic polymers are often observed (Coleman M R, et al., Isomeric polyimides based on fluorinated dianhydrides and diamines for gas separation applications. *J Membr Sci* 1990; 50:285-97). TADPS-based PBIs follow this meta/para isomer effect (Id.; Mi et al., *J Membr Sci* 1993; 77:41-8). Furthermore, whereas the permeabilities increase from TADPS-IPA to TADPS-TPA to TADPS-OBA, the selectivities decrease. For TADPS-OBA, the $H_2/CO_2$ selectivity was 10.1, which increased to 19.5 for TADPS-TPA and 32.2 for TADPS-IPA. A high $H_2/CO_2$ selectivity coupled with a $H_2$ permeability only moderately lower than those of TADPS-TPA and TADPS-OBA causes TADPS-IPA to cross both the prior $H_2/CO_2$ upper bound (initially reported in 1994) (Robeson et al., *Polymer* 1994; 35:4970-8) and the present upper bound (Robeson L M. The upper bound revisited. *J Membr Sci* 2008; 320:390-400).

TABLE 5

Ideal selectivities for TADPS-based polybenzimidazoles tested at 35° C. and 10 atm

| Samples | Ideal Gas Selectivity | | | | |
|---|---|---|---|---|---|
| | He/$H_2$ | $H_2/O_2$ | He/$O_2$ | $H_2/CO_2$ | $CO_2/O_2$ |
| TADPS-OBA | 1.2 | 33 | 38 | 10 | 3.2 |
| TADPS-TPA | 1.2 | 65 | 79 | 20 | 3.3 |
| TADPS-IPA | 1.4 | 67 | 94 | 32 | 2.1 |

Figure 10:
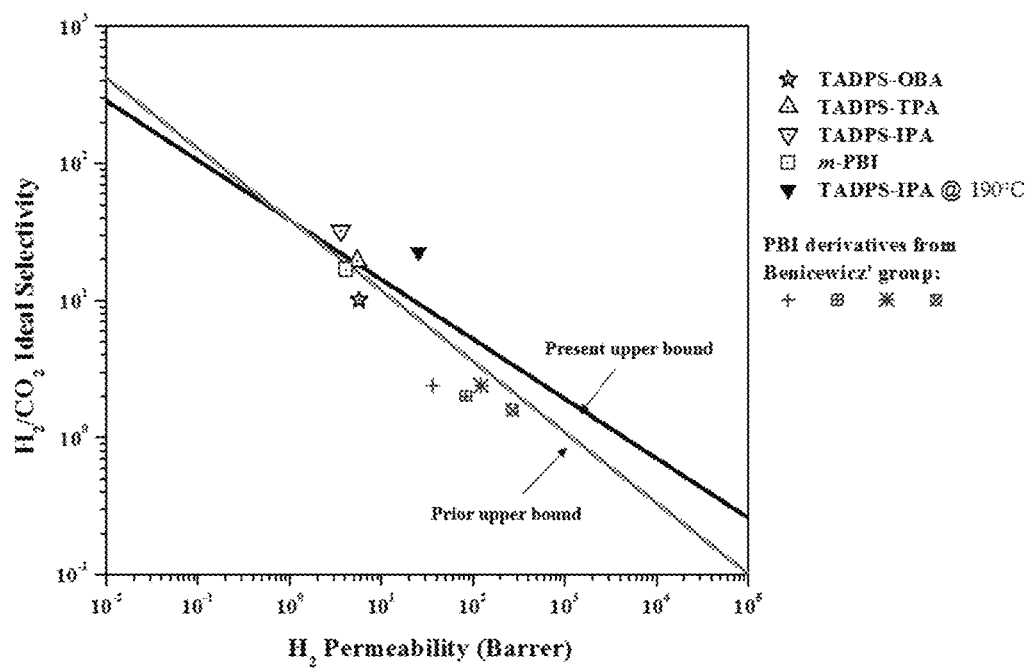
FIG. 10 shows the $H_2/CO_2$ upper bound plot comparison of TADPS-based polybenzimidazoles with other PBIs. The gas transport data is reported by Li et al. (Influence of polybenzimidazole main chain structure on $H_2/CO_2$ separation at elevated temperatures. *J Membr Sci* 2014; 461:59-68) for m-PBI measured at 43° C. and other PBI derivatives were measured at different temperatures in the range of 30-41° C.

In FIG. 10, the TADPS-based PBIs are plotted with the $H_2/CO_2$ upper bound to compare with m-PBI and other PBI derivatives reported by the Benicewicz group at near-ambient temperature (30-43° C.) (Li X, et al., Influence of polybenzimidazole main chain structure on $H_2/CO_2$ separation at elevated temperatures. *J Membr Sci* 2014; 461:59-68). By introduction of fluorinated bulky linkages from the diacid monomers into the PBI backbone, the PBI derivatives had much higher $H_2$ permeabilities than m-PBI (Id.). However, the $H_2/CO_2$ selectivities of these PBI derivatives were substantially lower than the m-PBI. As a result, the PBI derivatives still fell below the prior upper bound. Adding sulfonyl rather than fluorinated linkages in the tetraamine monomer did not significantly improve $H_2$ permeabilities compared with m-PBI. The TADPS-OBA polymer also shows a lower $H_2/CO_2$ selectivity, but the selectivities of TADPS-TPA and TADPS-IPA were enhanced.

The upper bounds reported by Robeson were based on experimental results of gas transport properties of existing polymers measured at ambient temperature (25-35° C.).

Freeman later provided the fundamental theory of the upper bound, which agreed well with empirical observations (Freeman et al., *Macromolecules* 1999; 32:375-80). Both Freeman et al. and Robeson et al. (An empirical correlation of gas permeability and permselectivity in polymers and its theoretical basis. *J Membr Sci* 2009; 341:178-85) showed that the slope of the upper bound is related to the ratio of the penetrant diameters and is unlikely to change as the state of the art develops. As mentioned by Robeson (Robeson L M. *J Membr Sci* 2008; 320:390-400), limited data are available at the low-permeability limit of the $H_2/CO_2$ upper bound. A more complete structure-property study of PBIs could contribute to this region of the upper bound plot.

It would be desirable to operate $H_2/CO_2$ separations at elevated temperatures for $H_2$ production from pre-combustion syngas (Merkel et al., *J Membr Sci* 2012; 389:441-50; Pesiri et al., *J Membr Sci* 2003; 218:11-8). TADPS-based PBIs are potential candidates for high temperature gas separation in part due to their thermal stabilities. Permeability obeys an Arrhenius-van't Hoff relation with temperature (Ghosal et al. *Polym Adv Technologies* 1994; 5:673-97). For $H_2/CO_2$ separation, Li et al. demonstrated that PBIs and their derivatives move toward the upper right and cross the upper bound as temperature increases (*J Membr Sci* 2014; 461: 59-68). TADPS-based PBIs show a similar behavior with temperature. The $H_2$ permeability and $H_2/CO_2$ selectivity of TADPS-IPA at 190° C. are shown in FIG. 10. As temperature increases, the permeabilities of both $H_2$ and $CO_2$ increase while selectivity stays relatively constant.

CONCLUSIONS 3,3',4,4'-Tetraaminodiphenylsulfone was synthesized via a novel route with fewer overall steps and improved yield relative to previously-reported methods, starting from an economical commercial monomer (dichlorodiphenylsulfone). A series of high molecular weight PBIs based on the 3,3',4,4'-tetraaminodiphenylsulfone monomer were synthesized by solution polymerization in Eaton's Reagent and their properties were compared to the commercial m-PBI (CELAZOLE™) and other PBI derivatives for $H_2/CO_2$ gas separation. The TADPS-based PBIs had increased glass transition temperatures and better organo-solubilities compared to m-PBI. Better solubility in organic solvents may likely be a major advantage since this may aid in solvent-casting thin, defect-free membranes. These TADPS-based PBIs were fabricated into films by solution casting for gas transport measurements. These TADPS-based PBIs exhibited good gas separation properties for $H_2/CO_2$ separation. TADPS-IPA and TADPS-TPA demonstrated a significant enhancement on the upper bound graph compared with m-PBI, and TADPS-IPA crossed both the prior and present upper bounds. Based on their attractive $H_2/CO_2$ transport properties, TADPS-based PBIs are promising candidates for further study.

The methods and compositions of the appended claims are not limited in scope by the specific methods and compositions described herein, which are intended as illustrations of a few aspects of the claims and any methods and compositions that are functionally equivalent are within the scope of this disclosure. Various modifications of the methods and compositions in addition to those shown and described herein are intended to fall within the scope of the appended claims. Further, while only certain representative methods, compositions, and aspects of these methods and compositions are specifically described, other methods and compositions and combinations of various features of the methods and compositions are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:
1. A polymer comprising Formula I:

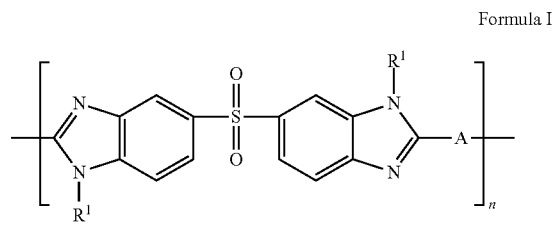

Formula I wherein
A is an aryl or heteroaryl containing moiety where the aryl containing moiety is chosen from one or more of

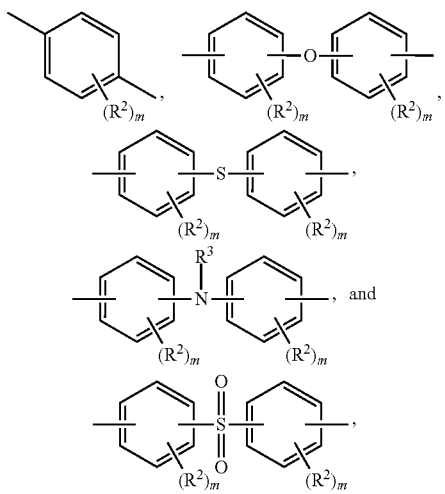

and the heteroaryl containing moiety is chosen from one or more of

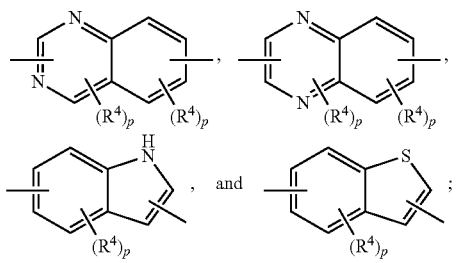

$R^1$ is H or substituted or unsubstituted $C_{1-20}$ alkyl, substituted or unsubstituted $COC_{1-20}$ alkyl, substituted or unsubstituted $CO_2C_{1-20}$ alkyl, substituted or unsubstituted $CO_2$ aryl, substituted or unsubstituted $CO_2C_{1-6}$ alkylaryl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, or mixtures thereof, wherein the substituted groups are substituted with one or more of alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol groups;

each $R^2$ is, independent of any other, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ alkoxyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, amino, hydroxyl, halide, or mixtures thereof, wherein the substituted groups are substituted with one or more of alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol groups;

$R^3$ is H, substituted or unsubstituted $C_{1-20}$ alkyl, or substituted or unsubstituted $COC_{1-20}$ alkyl, wherein the substituted groups are substituted with one or more of alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol groups;

each $R^4$ is, independent of any other, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ alkoxyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, amino, hydroxyl, halide, or mixtures thereof, wherein the substituted groups are be substituted with one or more of alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol groups;

each m is from 0 to 4;
each p is from 0 to 4; and
n is from 2 to 200,000.

2. The polymer of claim 1, wherein the polymer is a homopolymer.

3. The polymer of claim 1, wherein the polymer is a graft or block copolymer.

4. The polymer of claim 1, wherein A is the aryl containing moiety.

5. The polymer of claim 1, wherein A is the aryl containing moiety and is chosen from one or more of the following:

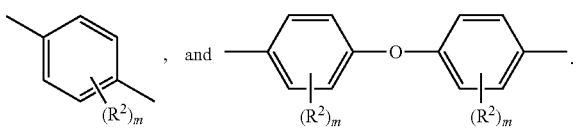

6. The polymer of claim 1, wherein m is 0.

7. The polymer of claim 1, wherein A is the heteroaryl containing moiety.

8. The polymer of claim 1, wherein $R^1$ is hydrogen.

9. The polymer of claim 1, wherein $R^1$ is $C_{1-6}$ alkyl, $COC_{1-6}$ alkyl, $CO_2C_{1-6}$ alkyl, $C_{1-6}$ haloalkyl, $COC_{1-6}$ haloalkyl, $CO_2C_{1-6}$ haloalkyl, $CO_2C_{1-6}$ aryl, or $CO_2C_{1-6}$ alkylaryl.

10. The polymer of claim 1, wherein the polymer comprises the formula:

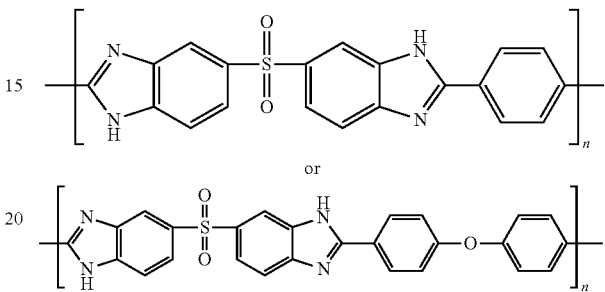

11. The polymer of claim 1, wherein the polymer is crosslinked.

12. A method of synthesizing a polymer, comprising: contacting 3,3',4,4'-tetraaminodiphenylsulfone with a polycarboxylic acid, salt thereof, or activated ester thereof, in the presence of phosphorus pentoxide and methanesulfonic acid, wherein the 3,3',4,4'-tetraaminodiphenylsulfone is synthesized by contacting dichlorodiphenylsulfone with a nitration reagent, to thereby provide a dinitrodichlorodiphenylsulfone, contacting the dinitrodichlorodiphenylsulfone with an amination reagent, to thereby provide dinitrodiaminodiphenylsulfone, and contacting the dinitrodiaminodiphenylsulfone with a reducing reagent, to thereby provide the 3,3',4,4'-tetraaminodiphenylsulfone.

13. The method of claim 12, wherein 3,3',4,4'-tetraaminodiphenylsulfone is contacted with an aryl or heteroaryl dicarboxylic acid, salt thereof, or activated ester thereof.

14. The method of claim 13, wherein 3,3',4,4'-tetraaminodiphenylsulfone is contacted with the aryl dicarboxylic acid, salt thereof, or activated ester thereof and the aryl dicarboxylic acid, salt thereof, or activated ester thereof is chosen from one or more of the following compounds:

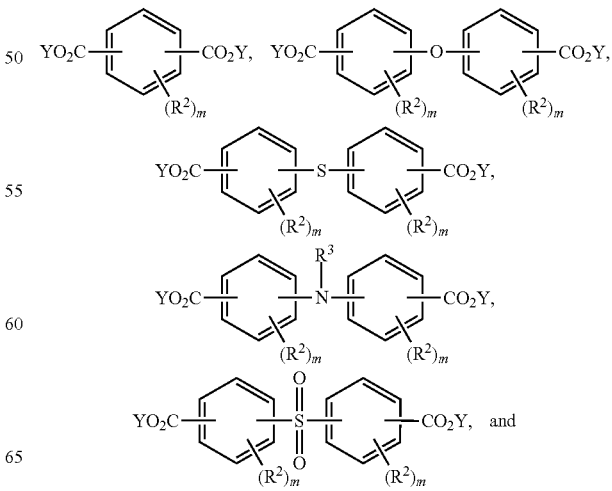

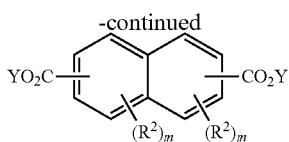

wherein
each R² is, independent of any other, substituted or unsubstituted C₁₋₂₀ alkyl, substituted or unsubstituted C₂₋₂₀ alkenyl, substituted or unsubstituted C₂₋₂₀ alkynyl, substituted or unsubstituted C₁₋₂₀ alkoxyl, substituted or unsubstituted C₁₋₂₀ heteroalkyl, substituted or unsubstituted C₂₋₂₀ heteroalkenyl, substituted or unsubstituted C₂₋₂₀ heteroalkynyl, substituted or unsubstituted cycloalkyl, substituted or unsubstituted heterocycloalkyl, substituted or unsubstituted aryl, substituted or unsubstituted heteroaryl, amino, hydroxyl, halide, or mixtures thereof, wherein the substituted groups are substituted with one or more of alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol groups;

R³ is H, substituted or unsubstituted C₁₋₂₀ alkyl, or substituted or unsubstituted COC₁₋₂₀ alkyl, wherein the substituted groups are substituted with one or more of alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol groups;

each m is from 0 to 4; and each Y is, independent of any other, H, Na, K, NH₄, succinimide, or carbodiimide.

15. The method of claim 14, wherein the aryl dicarboxylic acid is chosen from one or more of the following:

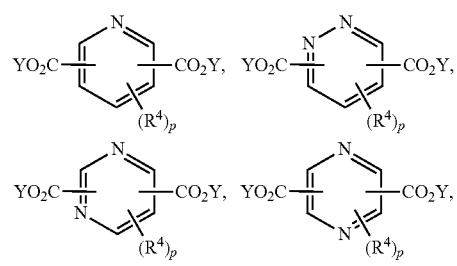

16. The method of claim 14, wherein m is 0 and Y is H.

17. The method of claim 13, wherein 3,3',4,4'-tetraaminodiphenylsulfone is contacted with the heteroaryl dicarboxylic acid, salt thereof, or activated ester thereof and the heteroaryl dicarboxylic acid, salt thereof, or activated ester thereof is chosen from one or more of the following compounds:

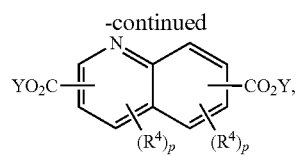
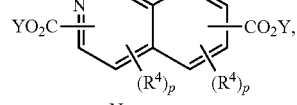
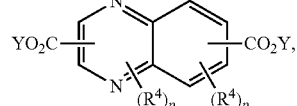
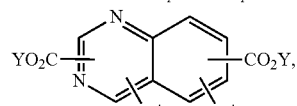
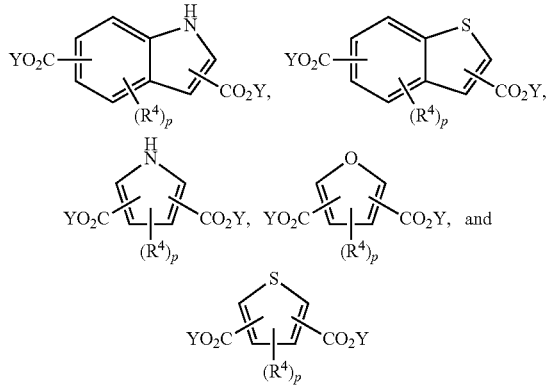

wherein
each R⁴ is, independent of any other, substituted or unsubstituted C₁₋₂₀ alkyl, substituted or unsubstituted C₂₋₂₀ alkenyl, substituted or unsubstituted C₂₋₂₀ alkynyl, substituted or unsubstituted C₁₋₂₀ alkoxyl, substituted or unsubstituted C₁₋₂₀ heteroalkyl, substituted or unsubstituted C₂₋₂₀ heteroalkenyl, substituted or unsubstituted C₂₋₂₀ heteroalkynyl, substituted or unsubstituted cycloalkyl, substituted or unsubstituted heterocycloalkyl, substituted or unsubstituted aryl, substituted or unsubstituted heteroaryl, amino, hydroxyl, halide, or mixtures thereof, wherein the substituted groups are substituted with one or more of alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol groups;

each p is from 0 to 4; and each Y is, independent of any other, H, Na, K, NH₄, succinimide, or carbodiimide.

18. The method of claim 12, further comprising cross-linking the polymer.

19. A method of synthesizing 3,3',4,4'-tetraaminodiphenylsulfone, comprising:
contacting dichlorodiphenylsulfone with a nitration reagent, to thereby provide a dinitrodichlorodiphenylsulfone;
contacting the dinitrodichlorodiphenylsulfone with an amination reagent, to thereby provide dinitrodiaminodiphenylsulfone;

contacting the dinitrodiaminodiphenylsulfone with a reducing reagent, to thereby provide 3,3',4,4'-tetraaminodiphenylsulfone.

20. The method of claim 19, wherein the nitration reagent comprises nitric acid, the amination reagent comprises ammonium, and the reducing reagent comprises hydrogen with a palladium catalyst.

21. A method of separating $H_2$ and $CO_2$ from a stream, comprising: contacting the stream with a polymer of claim 1.

* * * * *